(12) United States Patent
Zerkowski et al.

(10) Patent No.: US 11,219,524 B2
(45) Date of Patent: *Jan. 11, 2022

(54) SYSTEM AND A METHOD FOR DELIVERY OF AN ANNULOPLASTY IMPLANT

(71) Applicant: Medtentia International Ltd Oy, Espoo (FI)

(72) Inventors: Hans-Reinhard Zerkowski, Kreuzlingen (CH); Olli Keränen, Bjärred (SE); Ger O'Carroll, County Sligo (IE); Mark Pugh, County Sligo (IE); Adrian Moran, County Sligo (IE)

(73) Assignee: Medtentia International Ltd Oy, Espoo (FI)

( * ) Notice: Subject to any disclaimer, the term of this patent is extended or adjusted under 35 U.S.C. 154(b) by 250 days.

This patent is subject to a terminal disclaimer.

(21) Appl. No.: 16/296,089

(22) Filed: Mar. 7, 2019

(65) Prior Publication Data
US 2019/0201201 A1 Jul. 4, 2019

Related U.S. Application Data

(63) Continuation of application No. 15/119,702, filed as application No. PCT/EP2015/053421 on Feb. 18, 2015, now Pat. No. 10,251,749.
(Continued)

(30) Foreign Application Priority Data

Feb. 18, 2014 (EP) .................................. 14155506
Feb. 18, 2014 (EP) .................................. 14155508
Jul. 31, 2014 (EP) .................................. 14179416

(51) Int. Cl.
*A61F 2/24* (2006.01)

(52) U.S. Cl.
CPC .......... *A61F 2/2466* (2013.01); *A61F 2/2451* (2013.01); *A61F 2/2472* (2013.01); *A61F 2/2496* (2013.01)

(58) Field of Classification Search
CPC .... A61F 2/2496; A61F 2/2472; A61F 2/2451; A61F 2/2466; A61B 5/6855; A61B 5/6853
(Continued)

(56) References Cited

U.S. PATENT DOCUMENTS 10,321,989 B2 * 6/2019 Keranen ............... A61F 2/2427
2004/0127980 A1 7/2004 Kowalsky et al.
(Continued)

FOREIGN PATENT DOCUMENTS

JP 2008538937 A 11/2008
JP 2011506017 A 3/2011
(Continued)

OTHER PUBLICATIONS

WIPO, European International Search Authority, International Search Report and Written Opinion dated Jun. 25, 2015 in International Patent Application No. PCT/EP2015/053421, 9 pages.

*Primary Examiner* — George J Ulsh
(74) *Attorney, Agent, or Firm* — Inskeep IP Group, Inc.

(57) ABSTRACT

A delivery system and method for delivery of an annuloplasty implant for a patient are disclosed. The delivery system comprises a commissure locator device for locating a commissure, comprising; an extension member, a catheter, and wherein the extension member is extendable relative the catheter for location of at least one commissure of a cardiac valve, and a coronary sinus contractor for temporary insertion into the coronary sinus (CS) and having a displacement unit being temporarily transferable to an activated state in Which the shape of the annulus Of the heart valve is (Continued)

modified to a modified shape to be retained by said annuloplasty implant.

16 Claims, 10 Drawing Sheets

Related U.S. Application Data

(60) Provisional application No. 61/940,857, filed on Feb. 18, 2014.

(58) Field of Classification Search
USPC .......................................................... 623/2.11
See application file for complete search history.

(56) References Cited

U.S. PATENT DOCUMENTS

| | | | |
|---|---|---|---|
| 2005/0267574 A1* | 12/2005 | Cohn | A61F 2/2451 623/2.36 |
| 2006/0129051 A1* | 6/2006 | Rowe | A61B 1/00082 600/508 |
| 2006/0142854 A1* | 6/2006 | Alferness | A61F 2/2451 623/2.11 |
| 2009/0192603 A1 | 7/2009 | Ryan | |
| 2010/0280606 A1 | 11/2010 | Naor | |

FOREIGN PATENT DOCUMENTS

| | | |
|---|---|---|
| WO | WO2003/094801 A1 | 11/2003 |
| WO | WO2010/106438 A2 | 9/2010 |

* cited by examiner

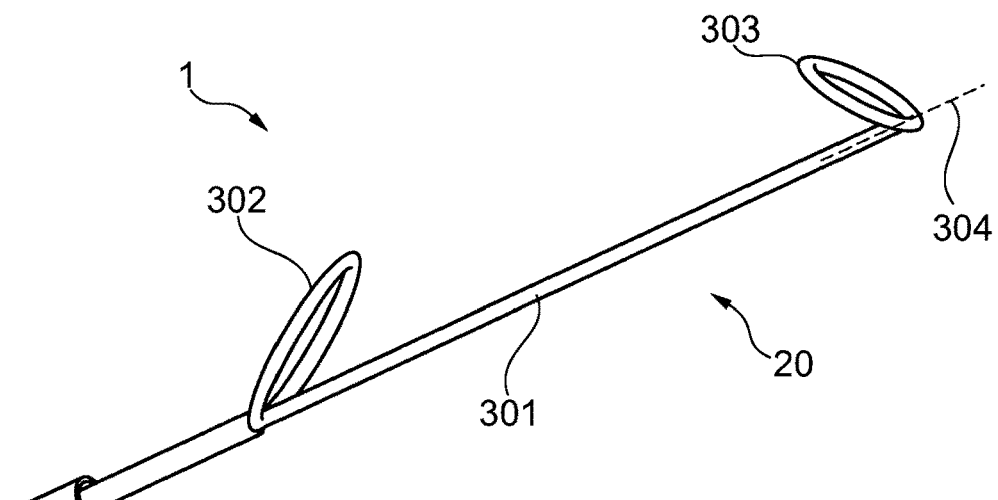
Fig. 2
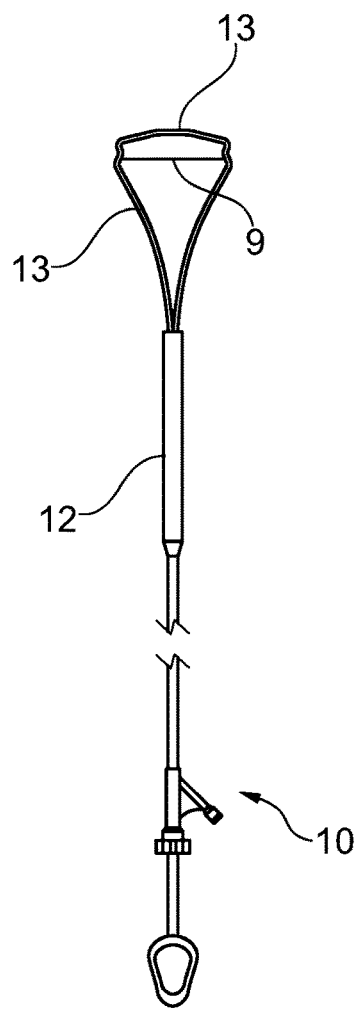
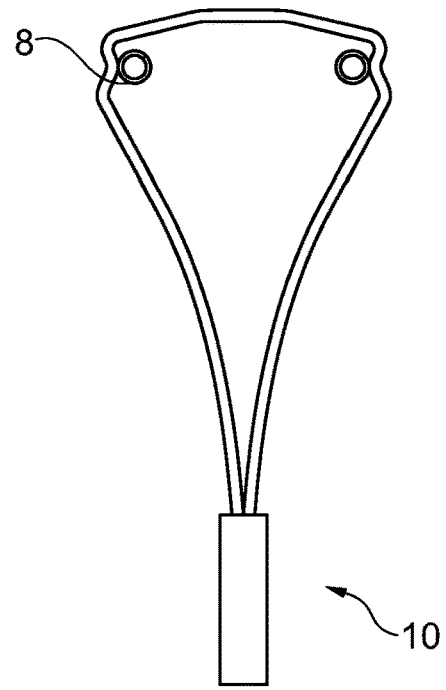
Fig. 1a        Fig. 1b

SYSTEM AND A METHOD FOR DELIVERY OF AN ANNULOPLASTY IMPLANT

RELATED APPLICATIONS

This application is a continuation of and claims priority to U.S. patent application Ser. No. 15/119,702 filed Aug. 17, 2016 entitled A System And A Method For Delivery Of An Annuloplasty Implant, which is the U.S. National Phase of International Patent Application No. PCT/EP2015/053421, International Filing Date Feb. 18, 2015 entitled A System And A Method For Delivery Of An Annuloplasty Implant, which claims benefit of and priority to U.S. Provisional Application Ser. No. 61/940,857 filed Feb. 18, 2014 entitled Steering System For Deployment And/Or Retrieval Of Interventional Heart Devices; European Patent Application No. 14155506.0 filed Feb. 18, 2014 entitled Stapling Device; European Patent Application No. 14155508.6 filed Feb. 18, 2014 entitled Medical Device For A Cardiac Valve Implant; and European Patent Application No. 14179416.4 filed Jul. 31, 2014, all of which are hereby incorporated herein by reference in their entireties.

BACKGROUND OF THE INVENTION

Field of the Invention

This disclosure pertains in general to the field of medical devices. More particularly the disclosure relates to a system for delivery of an annuloplasty implant.

Description of the Prior Art

It is known today that an annuloplasty implant for reshaping cardiac valves is of great importance to ensure greatest possible effect in the repair of the cardiac valve(s). A variety of tools to deploy the annuloplasty implant is known and they involve the use of a puncture device to gain entrance to the heart chamber and then a tool to for deploying the annuloplasty implant.

A problem with today's known technology is that the deploying of the annuloplasty implant is difficult and thus requires a long time which endangers the health of the patient.

A further problem of today's systems is the difficulty for the operator to quickly and with ease deploy the annuloplasty implant at its desired location without the need to use a trial and error approach. Further problems with today's systems include difficulties in positioning annuloplasty implants in a more accurate way.

Thus, there is a need for an improved system and method for delivering an annuloplasty implant.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a medical device and a method for use thereof that facilitates a selection of a size and/or shape of an annuloplasty implant, according to the appended patent claims.

According to aspects of the invention, a system and method for delivery of an annuloplasty implant are disclosed.

According to a first aspect of the invention, a delivery system is provided, the delivery system for delivering an annuloplasty system comprises a commissure locator device for locating a commissure, comprising an extension member, a catheter, and wherein the extension member is extendable relative the catheter for location of at least one commissure of a cardiac valve, and a coronary sinus contractor for temporary insertion into the coronary sinus (CS) and having a displacement unit being temporarily transferable to an activated state in which the shape of the annulus of the heart valve is modified to a modified shape to be retained by said annuloplasty implant.

According to a second aspect of the invention, a method of implanting an annuloplasty implant is provided comprising locating and substantially fixating the position the commissures of the heart valve by positioning a commissure locator device at the commissures, inserting a flexible and removable elongate displacement unit in a delivery state into a coronary sinus (CS) adjacent the valve, activating the displacement unit in an activated state whereby the shape of the annulus is modified to a modified shape, inserting said implant around the annulus of the heart valve, fixating said implant at the mitral valve annulus when the modified shape is obtained, removing the elongate displacement unit after temporary activation in the activated state.

Further examples of the disclosure are defined in the dependent claims, wherein features for the second and subsequent aspects of the disclosure are as for the first aspect mutatis mutandis.

Some examples of the disclosure provide for a delivery system having increased steerability or maneuverability.

Some examples of the disclosure provide for a delivery system having less time consuming positioning of an implant at a target site in the heart.

Some examples of the disclosure provide for a delivery system having less time consuming attachment and detachment of an implant to a medical device for efficient positioning and repositioning of such implant at the annulus.

Some examples of the disclosure provide for a delivery system having an increased accuracy in positioning an implant at the annulus and thereby reducing the risk of complications.

Some examples of the disclosure provide for a delivery system having a reduced risk of damaging the cardiac valve implant during a repair or replacement procedure.

Some examples of the disclosure provide for a delivery system having a better ability to retrieve and reposition an implant.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which FIGS. 1a-b are cross-sectional views of an example of a commissure locator device of a delivery system for delivery of an annuloplasty implant.

FIG. 2 is a view of an example of a coronary sinus contractor of a delivery system for delivery of an annuloplasty implant.

DESCRIPTION OF THE PREFERRED EXAMPLES

Figure 3:
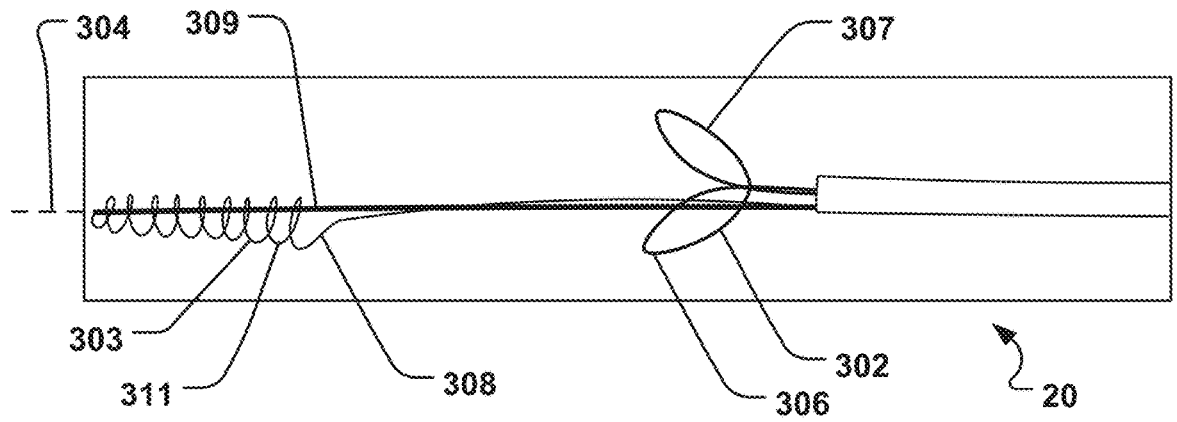
FIG. 3 is a view of an example of a coronary sinus contractor of a delivery system for delivery of an annuloplasty implant.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples in the accompanying drawings is not intended to be limiting of the disclosure. In the drawings, like numbers refer to like elements.

The following description focuses on an example of the present disclosure applicable to a medical delivery system and in particular to a medical delivery system for delivery of an annuloplasty implant.

Illustrated in FIGS. 1-2 is an example of a delivery system 1 for delivery of an annuloplasty implant. The delivery system 1 comprises a commissure locator device 10 for locating a commissure, and a coronary sinus contractor for temporary insertion into the coronary sinus (CS) and having a displacement unit 301 being temporarily transferable to an activated state in which the shape of the annulus of the heart valve is modified to a modified shape (A') (FIG. 5b) to be retained by the annuloplasty implant. The commissure locator comprises an extension member 13 and a catheter 12, and wherein the extension member 13 is extendable relative the catheter 12 for location of at least one commissure of a cardiac valve. By using the commissure locator device 10 and the coronary sinus contractor 20 the operator can in an easy and quick way find a desired location for implanting the annuloplasty implant and at the same time downsize the mitral valve so that the desired shape can be fixated by the implant that is guided into place by aid of the commissure locator device. This provides for in improved and secure fit of the annuloplasty implant to the mitral valve, and thereby increased patient safety when restoring the valve function. Thus a synergetic effect is obtained, since the downsizing provided by the coronary sinus contractor can be optimally utilized due to the exact and stable positioning of the implant provided by the commissure locator device (as described further below), and further, due to the stabilization of the valve anatomy provided by the commissure locator device, and improved positioning of the implant, the coronary sinus contractor will allow for a more controlled and user-definable amount of downsizing of the anatomy. The system 1, is further illustrated in FIG. 7, described further below.

Figure 7A:
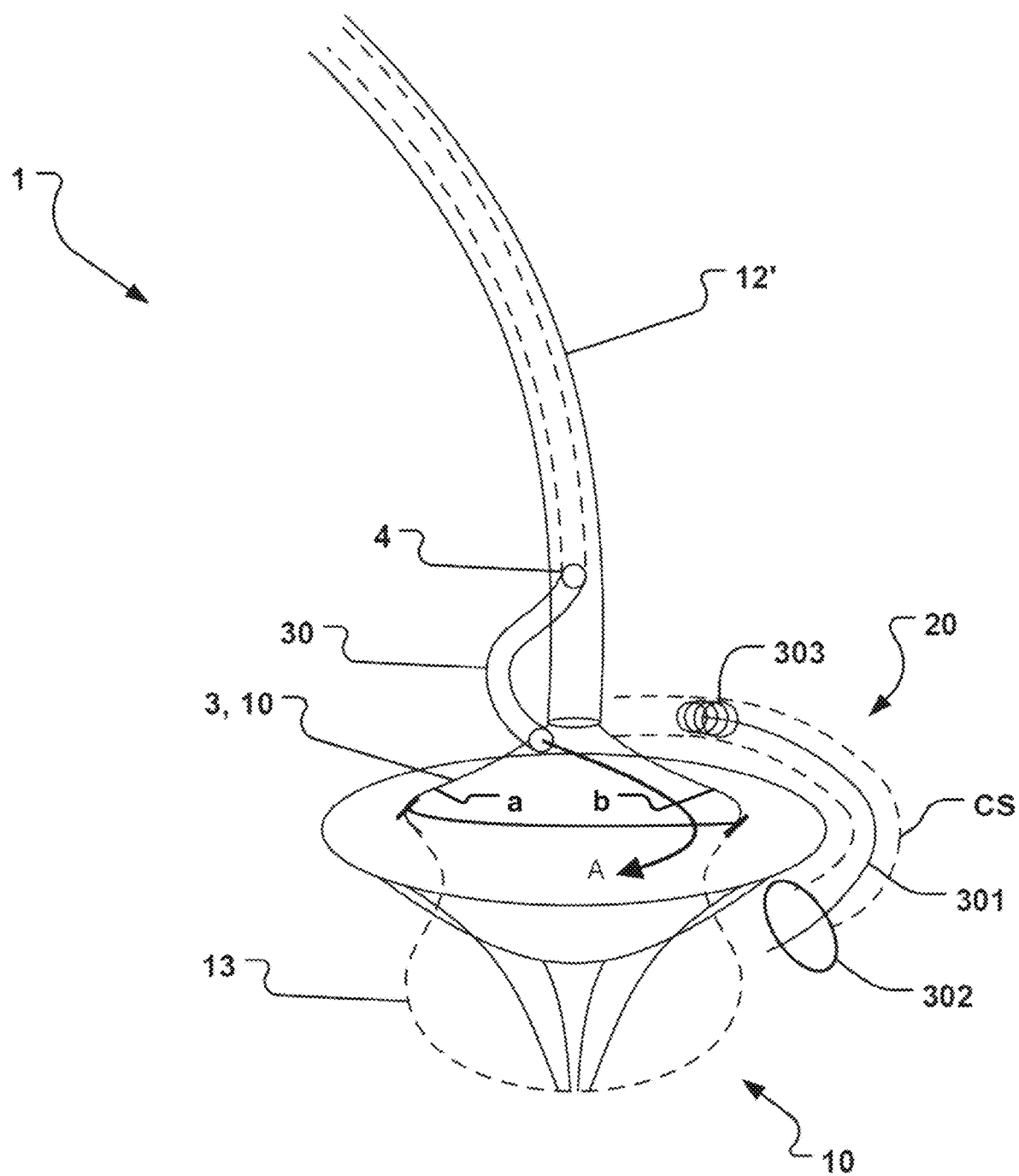
FIG. 7a is a view of an example of a commissure locator device and a coronary sinus contractor of a delivery system for delivery of an annuloplasty implant.
Figure 7B:
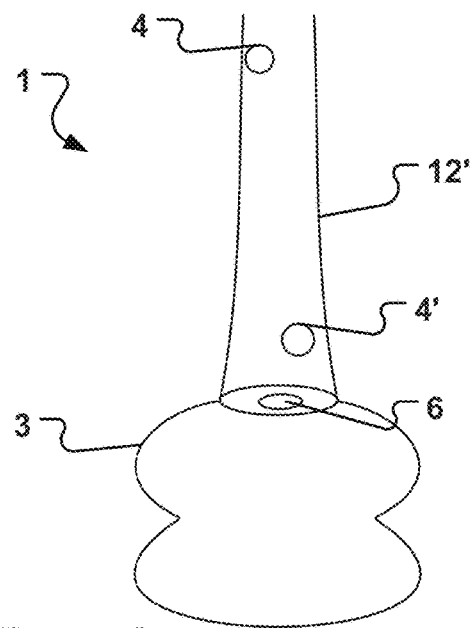
FIG. 7b-d are further views of an example of a commissure locator device.
Figure 7D:
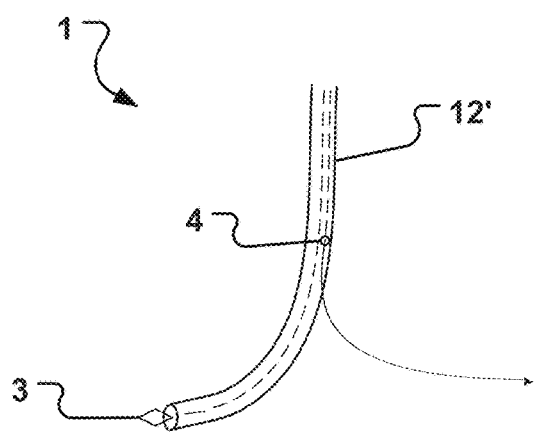
Figure 7C:
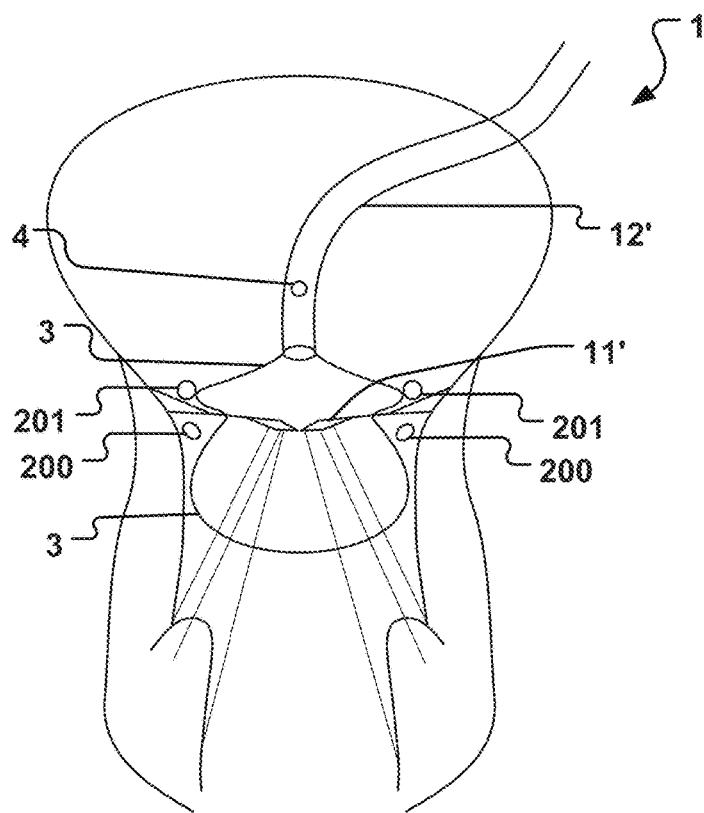
Figure 8:
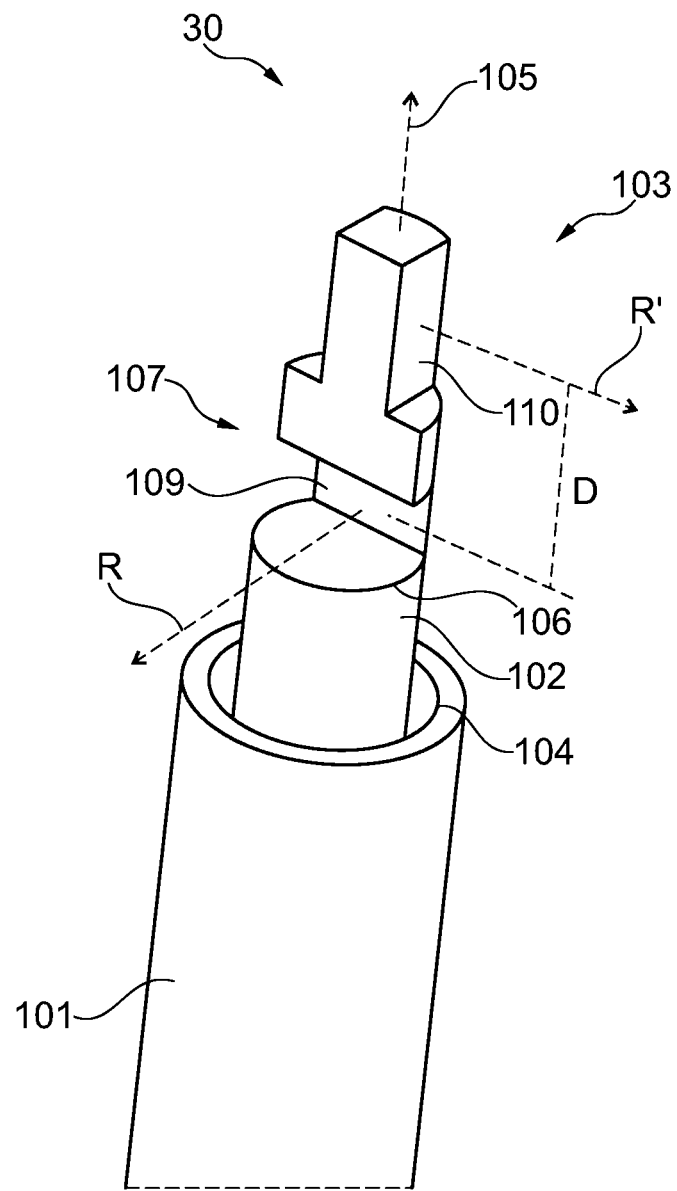
FIG. 8 is a view of an example of a delivery and retrieval device of a delivery system for delivery of an annuloplasty implant.

In an example, illustrated in FIG. 8 (and FIG. 7) the delivery system 1 also comprises an implant delivery and retrievable device 30. By using the implant delivery and retractable device 30 it is possible to also arrange the annuloplasty implant at the desired location at the mitral valve in a quick and easy way and if needed re-deploy the annuloplasty implant.

Figure 10:
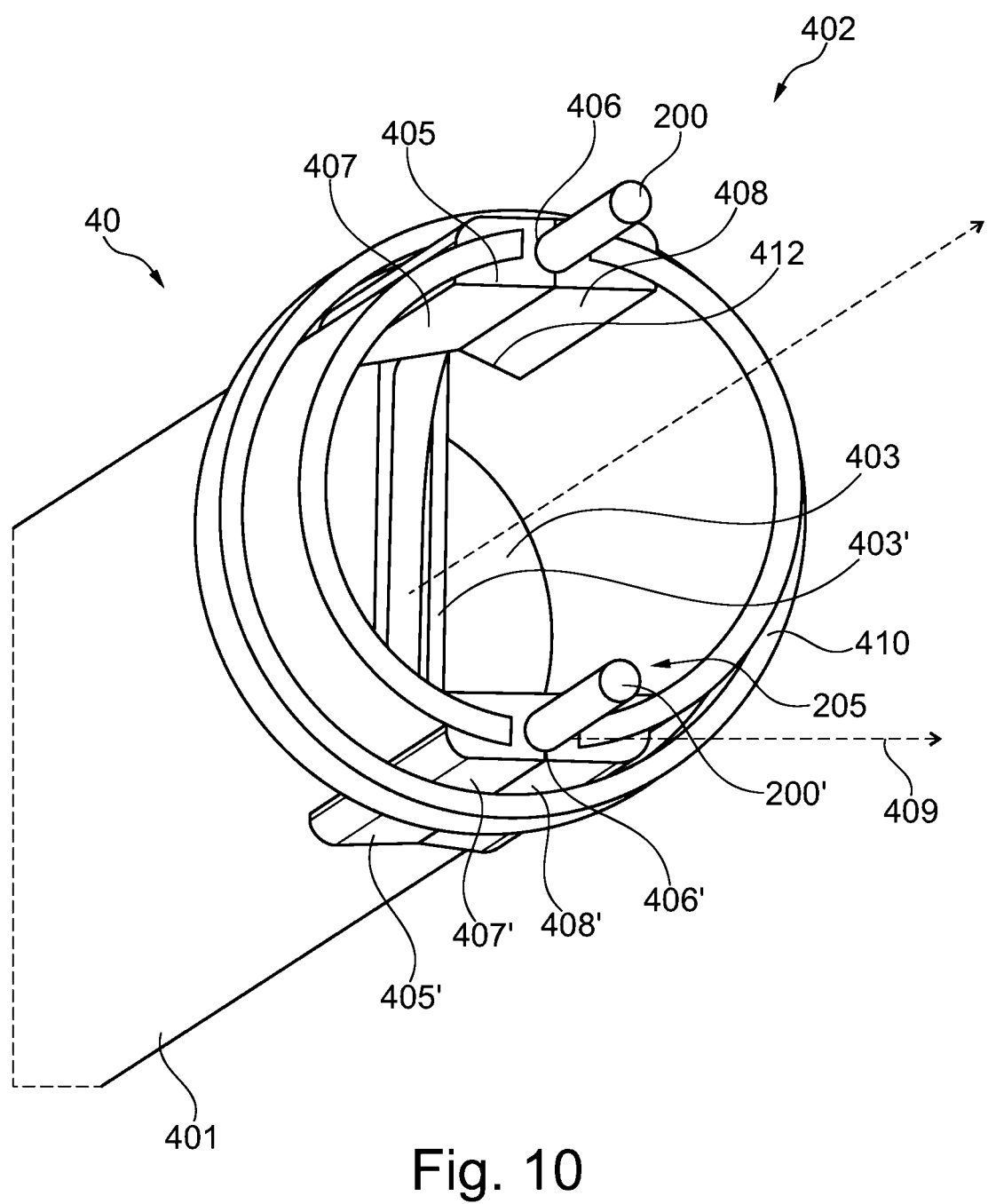
FIG. 10 is a cross-sectional view of an example of a stapling device of a delivery system for delivery of an annuloplasty implant.

In an example, illustrated in FIG. 10, the delivery system further comprises a stapling device 40 for final securement of the annuloplasty implant at the mitral valve. The stapling device 40 allows for easy and quick securement of the annuloplasty implant.

The following will give more examples of the individual components of the delivery system 1.

Commissure Locator Device

The commissure locator device comprises a catheter 12 with a proximal end and a distal end. The commissure locator device 10 further comprises an extension member 13 at least partly arranged inside the catheter 12 with an operator end and a measurement end and wherein the measurement end of the extension member 13 is extendable relative from the distal end of the catheter 12 for apposition with at least one commissure of a cardiac valve, such as a mitral valve of the patient and wherein a measure related to the selection of the annuloplasty implant shape and/or size is based on at least an extended length of the measurement end of the extension member 13 from the distal end of the catheter 12, positioned at the cardiac valve, to the at least one commissure. By use of the commissure locator device 10 providing the measure related to the selection of the shape and/or size of the annuloplasty implant an operator of the commissure locator device 10 is facilitated to in an easy and reliable way decide on the shape and/or size of the annuloplasty implant.

Catheter 12 used herein this disclosure is of well known types and wherein the catheter 12 is capable of comprising at least an extension member 13 according to this disclosure. Additionally the catheter 12 is capable of being rotated and/or otherwise steered into position at the cardiac valve from a desired position in or outside the body by the operator.

In an example the extension member 13 is a rod or alternatively a pole and/or another long thin member with a cylindrical, circular, squared or rectangular base, capable of being arranged in the catheter 12. In an example the extension member 13 is a rod extended perpendicular from the catheter 12 outwards towards the commissure. In another example the extension member 13 is of a semi-circular shape such as a leaf shaped and where the semi-circular shape is directed towards the at least one commissure and has a spring action for apposition to at least one commissure.

In another example of the extension member 13 the extension member 13 has an oval cone shape for apposition to at least one commissure. The oval cone shape is in example formed of at least one extending sheet. In another example the oval cone shape is formed from several braided, extending or interwoven shape members.

In another example the extension member 13 is rotationally arranged in the catheter 12 for apposition with the at least one commissure. In another example the extension member 13 is slidably arranged in the catheter 12. These arrangements allow for easy use and movement of the extension member 13 and catheter 12. Alternatively, the arrangement allows for easy use and movement independently of each other.

The extension member 13 is made of a suitable material compatible with and for use in a catheter 12 and in a heart, such as of titanium, nitinol, polymer, carbon fiber, textiles, all in solid forms or in braided or sandwich structure forms, etc. The extension member 13 has a length that is at least as long as the catheter 12 and a distance from the catheter 12 to the at least one commissure. The extension member 13 is preferably long enough to be operated at the operator end by the proximal end of the catheter 12 and still extendable at the measurement end at the distal end of the catheter 12, Le. the extension member 13 extends out of and from the catheter 12 at both ends of the catheter 12 when used by the operator.

In another example of the extension member 13 has a length wherein the measurement end of the extension member 13 only extends out and from the distal end of the catheter 12 and the operator end of the extension member 13 is arranged at level with the proximal end of the catheter 12, Le. the extension member 13 only extends from the catheter 12 at the distal end of the catheter 12 when used by the operator. By using the manoeuvrable extension member 13 the operator measures a distance from the catheter 12 at the cardiac valve to the at least one commissure and bases the size and/or shape of the annuloplasty implant on the distance.

In one example the measure related to the annuloplasty implant's shape and/or size is indicated at the operator end of the extension member 13. By having the operator end of the extension member 13 indicating the measure related to the size and/or shape of the annuloplasty implant, the operator can quickly and with ease visually see which annuloplasty implant the operator should choose.

Another example of the measurement end of the extension member 13 comprises two sections a, b, separable towards each of the mitral valve's commissures. By using two sections a, b, that are separable towards two commissures at the mitral valve a distance between the two commissures is measured immediately and faster than when using the extension member 13 without the two separable sections a, b.

In other example the two separable sections a, b, are upon extension from the catheter 12 aligned in a plane extending along a direction of the proximal end of the catheter 12. By having the two separable sections a, b, aligned and extended in the plane parallel to the direction of the catheter 12 the two sections a, b, will be easier to control due to their shared alignment with the direction of the catheter 12. This can be in b where the separable sections a, b, of the extension member 13 are separated perpendicular to the catheter 12.

Further, in yet another example the two separable sections a, b, separate with an opposite inclined separation angle. By having the two sections a, b, separate with opposite inclined angle of separation the two separable sections a, b, extend the same distance outwards towards the commissures and thus are easier to apposition with the two commissures due to their synchronised extension.

The two separable sections a, b, are in one example an integral continuation of the extension member 13. By having the two separable sections a, b, being the integral continuation of the extension member 13 the two separable sections a, b, better responds to manoeuvres, such as rotation and/or extension of the extension member 13 performed by the operator. Additionally, a requirement for manufacturing of the extension member 13 is greatly reduced since the extension member 13 and the two separable extensions are made in one piece. In one example the two separable sections a, b, and the extension member 13's mechanical aspects such as increased breaking resistance and/or improved rotational force, are greatly improved because the extension member 13 and the two separable sections a, b, are sized and/or shaped dependent on each other.

Alternatively, the two separable sections a, b, are joined to the measurement end of the extension member 13. By allowing the two separable sections a, b, to be joined at the measurement end of the extension member 13 they may be manufactured from a different material than the extension member 13 and thus have other material properties with respect to bending, rotation and/or biocompatibility.

In another example the extension member 13 comprises two separable sections a, b, which further comprises a c-shaped or claw shaped end. This claw shaped end is large enough to encompass an edge of a valve leaflet when aligned at the at least one commissure so that the extension member 13 is further secured at the at least one commissure.

In one example the commissure locator device 10 further comprises a force detection unit connected to the extension member 13 for detection of a manoeuvre force applied to the extension member 13. By using the force detection unit for detecting the manoeuvre force applied to the extension member 13 it is possible to get a further more reliable indication of when the extension member 13 is at apposition or in contact to or with at least one commissure.

In a further example of the extension member 13, the measurement end of the extension member 13 comprises anchoring means for attaching anchors at at least one commissure for the annuloplasty implant. Alternatively, one anchor is attached at one commissure. By having the extension member 13 comprising anchoring means for attaching anchors for the annuloplasty implant it is possible to detect the location of the at least one commissure and following the localization attach anchors at the commissure so that the annuloplasty implant can be anchored. This allows for fast deployment of the annuloplasty implant after the at least one commissure is found and the size and/or shape of the annuloplasty implant has been chosen. In an example the anchoring means is a claw or similar that allows for gripping the anchors.

In one example, the anchors comprise at least one guiding unit 8, as seen in FIG. 1b. By using at least one guiding unit or rings as anchors the annuloplasty implant, which preferably has the shape of a helix ring, is rotated into place at the cardiac valve by use of the anchors. For example, when using rings as anchors the annuloplasty implant is inserted through and slides in the rings securing the annuloplasty implant at the commissures. In an example the anchors are arranged in the atrium and catch and guides an upper part of the helix ring. In another example the anchors are arranged in the ventricle and catch and guides a lower part of the helix ring. In yet another example the anchors are arranged in both the atrium and the ventricle, and catch both parts of the helix ring and part of the annulus. This allows for the helix ring to be anchored in different ways from different entering points at the commissure and provides for stabilizing the helix ring at suitable locations.

As discussed above, in one example the anchoring means comprises anchors that are used as guides, i.e. guiding means, for the annuloplasty implant at the at least one commissure. In another example the anchors are used alternatively and/or in addition, as means for guiding the annuloplasty implant at the at least one commissure before the anchors may be attached at the at least one commissure. This allows the user to both measure the correct size of the annuloplasty implant and guide the annuloplasty implant into place in an easy way without removing the commissure locator device 10 when placed at the at least one commissure and at the same time avoid attaching the anchors at the at least one commissure, thus reducing the time for deploying the annuloplasty implant in the patient. In this example, the means for guiding is may be generally open or c-shaped which allows the annuloplasty implant to be guided into place in the heart without attaching the means for guiding at the at least one commissure and which allows for removal of the means for guiding, after the annuloplasty implant is implanted in the patient, through the opening of the c-shape. Thus the extension member 13 may comprise guiding means that are generally open or C-shaped for guiding an implant into place. Other shapes that can be used are substantially loop-shaped, triangle-shaped, ring-shaped, such as shown in a, or any other suitable shape that allows for guiding the annuloplasty implant into place and/or allows for removing the means for guiding when the annuloplasty implant is implanted in the heart. The extension member 13 may have guiding means at each the two lateral parts of the extension member 13 that are to be placed at the commissures.

In a further example of the extension member 13 the measurement end of the extension member 13 is shaped and/or formed as one coherent member. The extension member 13 may thus be formed as a continuous single or one-piece loop, Le. a closed design. By using the extension member 13 formed from one piece closed design the member is much more stable in its construction and easier to manoeuvre in the heart. Further, the continuous loop provides for particularly efficient stabilization of the anatomy and improving the precision by which the implant can be placed at the valve. Further, the continuous loop minimizes undesired interference with the chordae in the heart that would otherwise be the risk when having projections, edges, kinks etc. The extension member 13 may comprise a continuous loop having a distal portion being curved outwardly in a direction from the distal end of the catheter 12. Such curved shape further reduces the risk of damaging any chordae due the smooth shape. In the example in a, the distal portion bridges the two guiding means on the extension member 13. This provides for an atraumatic extension member 13 that effectively stabilizes the valve, while at the same time providing guiding means for the implant. The principle of use and mode of use is the same as for the other examples of extension member 13 described in this application. Hence, the measurement, expansion, material and so on are the same and operate in the same way.

In another example the extension member 13 comprises a leaflet limiter 9, FIG. 1a. The leaflet limiter is not limited to be used only with the coherent extension member 13 but the other types of extension member 13 disclosed in this application may also have the leaflet limiter. The leaflet limiter limits abnormal movement, such as prolapse, of the leaflets into the atrium. Such abnormal movement may arise if a chordae, or several chordae, that usually limits the movement of the leaflet is completely destroyed and the leaflet may thus freely move in the left atrium and/or left chamber. The leaflet limiter is made of a material that expands with the extension member 13, and it may be made of the same material as the extension member 13. The leaflet limiter may also be such that it can be bent, twisted or otherwise collapsed into the catheter 12 and then assume a desired shape when released from the catheter 12. Alternatively, the leaflet limiter is expanded by a spring back motion and/or force when exited from the catheter 12 with the extension member 13. The example of the leaflet limiter shown in FIG. 1a, is a crossbar that extends between two anchoring points of the extension member 13 and is projected laterally from an intersecting plane of the anchoring points of the extension member 13. The leaflet limiter may be of one piece or be made up of several pieces and/or have a number of different shapes and/or have various placements. One example of a shape that limits but not damage the leaflet(s) when hindering the movement into the atrium would be to have a simple straight projection outwards towards the leaflets from the extension member 13 with a blunt end, which can limit the movement but not damage the leaflet(s) when hindering the movement into the atrium. Preferably, the extension member 13 has two leaflet limiters, one on each side of the extension member 13 for each leaflet when the extension member 13 is arranged at the commissures. But, there could also be only one leaflet limiter. This could be the case if it is known that one leaflet is already damaged and moving freely when starting the procedure of measuring and/or deciding the size of the annuloplasty implant.

In an example according to the disclosure a method for facilitating selection of a shape and/or size of an annuloplasty implant is disclosed. The method comprises providing a commissure locator device 10 such as the commissure locator device 10 for facilitating the selection of a shape and/or size of an annuloplasty implant as described above. The method further comprises positioning, preferably minimally invasively, a distal end of the catheter 12 of the commissure locator device 10 at a cardiac valve of a patient. The method further comprises extending a measurement end of an extension member 13 relative from a distal end of the catheter 12, bringing the measurement end in apposition with at least one commissure of the cardiac valve, such as a mitral valve of said patient. The method also comprises basing the annuloplasty implant's shape and/or size on at least an extended length of the extension member 13 relative from the distal end of the catheter 12 to the at least one commissure. By using the commissure locator device 10 for facilitating the selection of the shape and/or size of the annuloplasty implant comprising the catheter 12 and the extension member 13 it is possible to base the size/and or shape of the annuloplasty implant on the extension of the extension member 13 relative from the catheter 12.

In one example, the catheter 12 is positioned in a substantially centre position at the cardiac valves. Following the extension member 13 is extended from the distal end of the catheter 12 by an operator pushing the extension member 13 from the proximal end of the catheter 12 through the catheter 12 and out at the distal end of the catheter 12. The measurement end of the extended extension member 13 is positioned at, appositioned, or in contact with the commissure.

The positioning of the extension member 13 is performed in a number of way such as by rotating the extension member 13 relative to the catheter 12, sliding the extension member 13 inside the catheter 12, by synchronised movement of the catheter 12 and the extension member 13 and/or by synchronised movement of the catheter 12 and the extension member 13 where the extension member 13 and the catheter 12 is engaged so that when movement of the catheter 12 is performed the extension member 13 is moved in the same way as the catheter 12.

The extended length of the extension member 13 from the substantially centre position to the commissure gives the operator a measure on the size and/or shape of the annuloplasty implant. The extended length is in one example used as basis for the radius of the annuloplasty implant. In another example an assumption that the cardiac valve is symmetrical together with the extended length of the extension member 13 is used as basis for the width of the annuloplasty implant.

In another example of the method for facilitating selection of a shape and/or size of an annuloplasty implant the basing of the annuloplasty implant's shape and/or size is based on a measured valve width between two commissures of the cardiac valve by the extension of the measurement end of the extension member 13 relative from the catheter 12 to the two commissures. Basing the selection of the annuloplasty implant on the distance between the two commissures gives a better fit of the annuloplasty implant than when only using one commissure. In one example the width between the two commissures are measured by sweeping the extension member 13 from one commissure to the other commissure.

In another example the width is obtained between the two commissures by arranging of two separable sections a, b, of the extension member 13 separable towards the commissures. The use of the extension member 13 comprising two separable sections a, b, separable towards the commissures results in the width between the commissures being measured more accurately and faster than any presently known method. When obtaining the width between the commissures by use of the extension member 13 comprising two separable sections a, b, the operator positions the catheter 12 at the cardiac valve and extends the extension member 13. The two separable sections a, b, separate outwards towards the commissures when they passes the distal end of the catheter 12 by the operator pushing the extension member 13 through the catheter 12 from the proximal end of the catheter 12. Depending on the pushed distance of the extension member 13 Le. extended distance of the extension member 13 and the two separable sections a, b, the width of the commissures is known. The separation of the two separable sections a, b, is preferably at a predefined angle and/or settles at the predefined angle when measuring the width between the commissures. The extension of the extension member 13 from the catheter 12 may be performed in several ways such as, out from the proximal end of the catheter 12 and/or out through the sidewall of the catheter 12 at the proximal end.

In one example the method further comprises measuring an applied manoeuvre force on the extension member 13 while maneuvering the extension member 13 to apposition the measurement end with the at least one commissure and, indicating when the measurement end is apposition with the at least one commissure based on the measured applied manoeuvre force. By measuring the applied manoeuvre force on the extension member 13 applied by the operator the indication of when at least one commissure has been found is performed more reliable than by use of tactile indication through the extension member 13. The measurement of the applied manoeuvre force may e.g. be measured by a force detection unit.

In one example if the force detection unit is used, the force detection unit bases the indication of the apposition to the at least one commissure by comparing the measured applied manoeuvre force with a predefined commissure value for triggering the indication of the apposition of the measurement end with the at least one commissure.

In another example of the method for facilitating selection of a shape and/or size of an annuloplasty implant an indication is based on a measured force for stretching the extension member 13 between two commissures. By measuring the force needed to extend and/or stretch the extension member 13 outwards towards the two commissures it is possible to detect when the two commissures have been found since the two commissures have a difference in flexibility compared to other tissue in the atrium.

In yet another example the method comprises anchoring at least one anchor at at least one commissure by use of the extension member 13 comprising anchoring means. By using at least one anchor at at least one commissure by using the extension member 13 the operator can attach anchors for the annuloplasty device in one go and with the same device, saving time compared to needed to use a second instrument for attaching anchors. In one example the anchoring means comprises anchors, or guiding means, that are used as guides for the annuloplasty implant at the at least one commissure. In another example the anchors are used alternatively and/or in addition, as means for guiding the annuloplasty implant at the at least one commissure before the anchors are attached at the at least one commissure. This allows the user to both measure the correct size of the annuloplasty implant and guide the annuloplasty implant into place in an easy way without removing the commissure locator device 10 when placed at the at least one commissure and at the same time avoid attaching the anchors at the at least one commissure, thus reducing the time for deploying the annuloplasty implant in the patient. In this example, the means for guiding is preferably c-shaped which allows the annuloplasty implant to be guided into place in the heart without attaching the means for guiding at the at least one commissure and allows for removal of the means for guiding after the annuloplasty implant is implanted in the patient through the opening of the c-shape. Other shapes that can be used are loop-shaped, ring-shaped or any other suitable shape that allows for guiding the annuloplasty implant into place and/or allows for removing the means for guiding when the annuloplasty implant is implanted in the heart.

Delivery and Retrieval Device

Figure 9A:
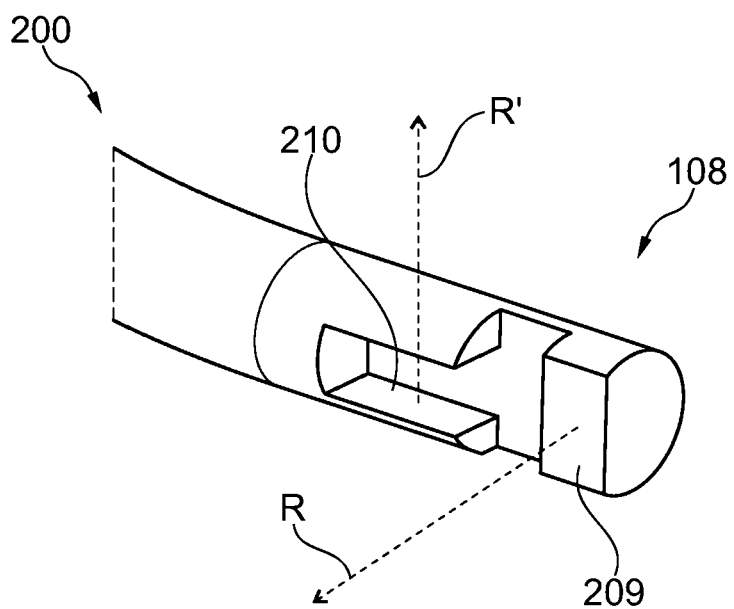
FIGS. 9a-b are views of an example of an annuloplasty implant for delivery with a the delivery system.
Figure 9B:
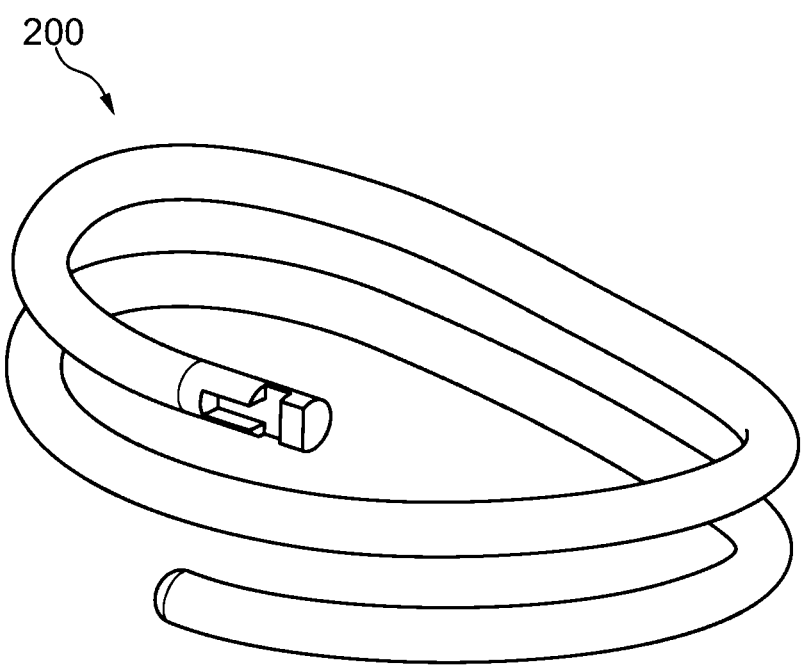

The medical implant delivery and retrieval device 30 is illustrated in FIGS. 7-9, and comprises a sheath 101, a wire 102 having a distal end 103 and being movable in a lumen 104 of the sheath 101 in a longitudinal direction 105 of the sheath. The distal end 103 comprises a locking structure 107 for receiving and interlock with a complementary mating surface 108 of a medical implant 200, such as shown in FIGS. 9a-b. The locking structure 107 comprises a first locking surface 109 aligned in a first radial direction (R) (indicated by dashed arrow in FIG. 8) to lock rotational movement of the implant 200, when received in the locking structure 107, around the longitudinal direction 105, Le. around the longitudinal axis 105. The locking structure 107 comprises a second locking surface 110 aligned to face a second radial direction (R'), different from the first radial direction (R), to lock movement of the implant 200, when received in the locking structure 107, transverse to the longitudinal direction 105. The second locking surface 110 thereby prevents movement of an implant 200 in a transverse direction, such as in the second radial direction (R') while the first locking surface 109 hinders the implant from rotating around axis 105. The implant 200 have a complementary mating surface 108 comprising first 209 and second

210 locking surfaces that are positioned opposite, i.e. parallel with, first 109 and second 110 locking surfaces of the device 100. By having two locking surfaces 109, 110, in facing different radial directions, the implant 200 can be effectively held in place by the device 100 without dislocating when handling of the implant. For example, torque can effectively be transmitted from the wire 102 to the implant 200, due to the first locking surface 109, while the implant 200 can be kept securely in the central position relative the longitudinal axis 105, I.e. co-axially positioned relative axis 105 due to the second locking surface 110 fixating the implant 200 in the transverse direction relative longitudinal axis 105, such as in the radial direction. This provides for improved maneuverability of the implant 200 since it is kept in a well-defined secure position relative wire 102 without undesired movement relative the latter. The second locking surface 110 provides for fixating the position in several directions transverse to the longitudinal axis 105, I.e. any transverse direction which has an angle towards the second locking surface 110, I.e. not parallel to the second locking surface 110. The second locking surface 110 provides for secure retrieval of the implant 200 if repositioning or any other adjustments becomes necessary during the procedure, since the position of the implant in the radial direction can be controlled, e.g. in the direction (R') or any other transverse direction with a vector component in a radial direction to the longitudinal axis 105. By securing the position in the radial direction, the implant 200 can be easily withdrawn into sheath 101, for removing the implant or just keeping the implant in the longitudinally locked position as described further below. In this example, if the position of the implant 200 is not secured in a second radial direction, as provided by the second locking surface 110, it will be more difficult or impossible to withdraw the implant 200 into the sheath 101. It should be noted that the first locking surface 109, besides from preventing rotational movement of the implant 200, also stops movement of the implant 200 in a radial direction, different from the (second) radial direction in which the second locking surface 110 stops movement. A radial direction in this disclosure should be construed as directions having any angle of 0-360 degrees around the longitudinal axis 105. For example, if the first locking surface 109 is aligned to face a radial direction (R) of 0 degrees, then the second locking surface may be aligned to have a radial direction (R') of 90 degrees as exemplified in FIG. 8.

The locking structure 107 may comprise a recess 106 adapted to interlock with the complementary mating surface 108 to lock longitudinal movement of the implant 200, when received in the locking structure 107, along the longitudinal direction 105. Recess 106 mates with a corresponding protrusion of the complementary mating surface 108 to fixate the position along the longitudinal axis 105. This further provides for improving control of the positioning of the implant 200 in the device 100 in order to accurately deliver, manipulate, and possibly retrieve the implant 200 during a procedure. The recess 106 allows the implant 200 to be drawn into the sheath 101. The locking structure 107 may thus be arranged to receive the complementary mating surface 108 when the locking structure extends outside the sheath 101, and to interlock with the complementary surface 108 and fixate the position of the implant 200 relative the locking structure 107 when the locking structure is retracted within the sheath 101. Hence, when in the withdrawn position, the sheath 101 restricts movement of the implant 200 in a radial direction in which the implant was received into the locking structure 107 in the extended position.

The first (R) and second (R') radial directions may be substantially perpendicular. This may provide for a more optimal locking engagement with the implant 200, as the first and second locking surfaces 109, 110, thereby complements each other in restricting movement in any radial vector component which is not parallel to any of the surfaces. Even if non-perpendicular locking surfaces 109, 110, would also cover all angles of movement, a perpendicular arrangement may make the connection between the locking structure 107 and the complementary mating surface 108 of the implant 200 easier. The second radial direction (R') may be perpendicular to both the first radial direction (R) and the longitudinal axis 105. The second locking surface 110 may however also form an angle relative the longitudinal axis (not shown), e.g. so that the surface 110 is part of a tapered distal portion of the locking structure 107. If the distal portion is tapered towards the implant 200 it may allow for easier guiding of the implant 200 into the distal portion of the locking structure 107, while at the same time providing for locking transverse movement when interlocked as described above. Alternatively, or in addition, the second radial direction (R') may have any angle relative the first radial direction (R).

The locking structure 107 may be open radially outwards to receive the complementary mating surface 108 in a radial direction. This provides for convenient interlocking with the implant 200 since the implant can be approached from the side and guided radially inwards.

The first and/or said second locking surface 109, 110, may be substantially flat. Hence, while the locking structure 107 provides for controlled fixation of the implant 200 the mating surfaces of the locking structure 107 and the implant 108 have a minimum of connecting portions that must be aligned, that also makes interlocking easier, and particularly of subsequent retrieval of the implant 200 is necessary.

Alternatively, or in addition, the first and/or said second locking surface 109, 110, may be curved or comprise a curved portion. The locking surface may have a sinusoidal shape, however it may also be possible to have any concave or convex shape, or a combination thereof. The implant 200 will in this example have a corresponding complementary curved shape. The surface of the curved portion has a normal direction (perpendicular to the tangent of the curve) that points in varying radial directions.

The first locking surface 109 may be continuous with the second locking surface 110. The implant 200 can be easier to capture and retrieve if there is a smooth path for the implant to follow when being positioned in the interlocked state. A continuous locking surface may look in several directions while allowing an implant to slide into position. The first and second locking surfaces 109, 110, may be overlapping in the longitudinal direction 105. This provides for a simplified locking structure 108 that may be easier to use and manufacture. The first and second locking surfaces 109, 110 may thus be provided as a single surface.

The first and second locking surfaces 109, 110, may also be displaced a distance (D) in relation to each other in the longitudinal direction 105. This may provide for better stability in the longitudinal direction 105 since the implant 200 is locked at each locking surface 109, 110, along the longitudinal direction 105. It may thus require a larger force to accidentally angle the implant relative the longitudinal direction 105.

The second locking surface 110 may be a recess in the first locking surface 109. The recess will have a surface facing a second radial direction (R') different from a first radial direction (R). Accordingly, the recess will be effective in stopping rotational movement and also movement transverse to the longitudinal direction 105, when interlocking with a corresponding mating surface of the implant 200, Le. a protrusion. Alternatively or in addition the second locking surface 110 may also be protrusion in the first locking surface 109.

The wire 102 may comprise a pivotable locking portion having a closed and an open position. The closed position of the pivotable locking portion locks movement of the implant 200, when received in the locking structure 107, in a radial direction. The radial direction may be the first radial direction (R). Since the first locking surface 109 faces the first radial direction (R), it may be desirable to fixate the position of the implant 200 in the direction of the normal to the first locking surface 109. This allows the implant 200 to be fixated in all direction without having to retract the locking structure 107 inside the sheath 101. Further, the pivotable locking portion 113 may grab the implant 200 if it's going to be retrieved. This may facilitate engagement of the implant and locking the implant 200 into the correct position before retracting the implant inside the sheath 101, or to get a stable hold of the implant before it is repositioned at the target site. The pivotable locking portion may also be arranged to lock the position in the second radial direction (R') or in any other radial direction. The pivotable locking portion may be mounted to rotate around a pivoting axis at the wire, and may be engaged with a separate locking wire (not shown) to be moved between the closed and the open position with an angle. In one configuration the locking portion has a locking structure with a recess with a first locking surface, and also a second locking surface, that engages with a complementary mating surface of the implant. Hence, instead of having the locking surface at the distal end of the wire, it may be provided at the pivotable locking portion. The distal end of the wire that receives the implant may have a recess, such as a partly cylindrical portion which receives a corresponding cylindrical portion of the implant. This may allow the implant to easily engage with the wire before locked into position by the pivotable locking portion. In an alternative arrangement the second locking surface may be omitted. The first locking surface of the pivotable locking portion mates with the implant to fixate the position in the longitudinal direction, and to stop rotational movement of the implant, while the recess of the wire, such as a partly cylindrical portion, hinders movement of the implant in a direction transverse to the longitudinal direction, e.g in a direction perpendicular to the longitudinal direction and the first radial direction (R). This may allow easy fixation of the implant while maintaining stability.

The medical implant delivery and retrieval device 100 may comprise a retrieval element (now shown) connecting the locking structure 107 and the implant 200 when the implant is disconnected from the locking structure 107. The retrieval element may hence serve as a security wire that can be engaged to retract the implant towards the locking structure 107 if desired. This may allow for easier navigation of the implant 200 towards the locking structure 107 and improving the security of the procedure.

Alternatively or in addition, the locking structure 107 may comprise an element (not shown) for attracting the implant 200 with a force, such as a magnet. Also, the magnet force may be switchable to an off state that may ease detachment of the implant 200 from the locking structure. The implant may also be pushed away from the magnet with a pusher (not shown) that is movable within a lumen of the locking structure 107 and exiting and extending beyond a distal end thereof, in order to again disengage the implant 200 after being captured with the magnet. Insertion of such pusher in the locking structure may disengage the first and/or second locking surfaces from the implant 200.

The sheath 101 may be steerable or shaped to allow for an improved delivery and/or retrieval angle of the implant 200, so that it can be more easily and accurately positioned. The sheath 101 may have a delivery configuration where it extends along a 3-dimensional path to position its distal end at a defined angle. Thus, the sheath 101 may assume a desired curve shape to optimize the positioning of the implant such as an annuloplasty ring or helix. The resulting angle from which the implant 200 can be delivered may thus be flat and close to parallel with respect to the valve, which allows for accurate positioning and easy insertion of the implant 200 when it exits the sheath 101. The implant 200 may be shaped from a flexible alloy such as Nitinol, and it is pre-shaped by heat treatment to assume a desired shape when exiting the sheath or catheter 101. In addition the implant 200 may comprise an atraumatic tip at its distal end, such as a partly spherical portion, to avoid damaging the tissue.

A kit is disclosed according to one embodiment comprising a medical implant delivery and retrieval device 100, and an annuloplasty implant 200 such as an annuloplasty ring or helix, wherein the annuloplasty implant 200 comprises the complementary mating surface 108 at an end portion thereof for interlocking with the locking structure 107 the medical implant delivery and retrieval device 100.

An annuloplasty implant 200 is disclosed according to one embodiment, see FIGS. 9a-b, such as an annuloplasty ring or helix comprising complementary mating surface 108 at an end portion thereof for interlocking with a locking structure 107 of a medical implant delivery and retrieval device 100 extending along a longitudinal direction 105. The mating surface 108 comprises a first locking surface 209 aligned in a first radial direction (R) to lock rotational movement of the implant 200, when received in the locking structure 107, around the longitudinal direction 105. The mating surface 108 comprises a second locking surface 210 aligned to face a second radial direction (R'), different from the first radial direction (R), to lock movement of the implant 200, when received in the locking structure 107, transverse to the longitudinal direction 105. The complementary mating surface 108 may be shaped to mirror any shape such as described above for the locking portion 107 of the device 100.

The system for deployment and/or retrieval of an implant, according to an example of the invention is further illustrated in FIG. 7a. The catheter 12' has a proximal end and a distal end and the catheter 12' is configured to be positionable within a heart adjacent to a cardiac valve. The system further comprises a coupling device 3 arranged at the distal end of the catheter 12' which comprises a coupling member configured to engage at least one pre-determined cardiac structure for coupling and aligning the catheter 12' in a known direction in the heart. The coupling device 3 may comprise the commissure locator device 10 having extension member 13 as described above for locating and positioning at the commissures for fixation and/or stabilization of the same. The catheter 12' may have at least one angled side port 4, between the proximal end and the distal end of the catheter 12', adapted for the interventional device such as an implant 200 (not shown), to pass through from an interior of the catheter 12' to an exterior of the catheter 12', or vice versa, and for steering the implant, to a desired target point A in the heart. The delivery and retrieval device 30, holding the implant 200, may thus pass through the side opening 4.

By using a catheter 12' with at least one angled side port 4 and the catheter 12' having a coupling device 3 arranged at its distal end it is possible to align and anchor the catheter 12', by use of the coupling device, relative to any cardiac structure in the heart. This allows for any interventional device, to be deployed and/or retrieved through the angled side port with a high accuracy of reaching and/or hitting a preferred target point A in the heart. Such interventional devices, may be selected from the group consisting of suturing devices, stapling device 40 (as shown in FIG. 10), radiofrequency electrodes, suctioning devices, grasping or delivery devices such as the device 30 (FIG. 8), annuloplasty implants 200 and/or other tools used for interventional cardiac procedures. In one example, an additional port 6 is arranged at the distal end of the catheter 12' for straight access for the interventional device, see FIG. 7b. The catheter 12' in FIG. 7b has two angled side ports 4, and 4', for deployment or delivery of tools or implants. Any number of side ports may be used, depending on the application.

Cardiac structures which may be utilized for coupling include the atrial walls, inter-atrial septum, valve annulus, valve leaflets, valve commissure's, valve chordae, papillary muscles and ventricle walls. Preferably at least one commissure of the cardiac valve, is utilised. By using the commissure or commissures, it is possible to use an easily reached and recognisable structure in the heart for alignment and securement of the steering system since the commissure (s) is protruding from the heart wall, and is shaped like a wedge, between the leaflets thus allowing the steering system to be aligned in a predetermined way.

The at least angled side port is in one example angled towards the cardiac structure in the heart. By angling the side port in a direction towards the cardiac structure that is of interest A, the interventional device, will be steered and hit this target point A with ease and a high accuracy since the catheter 12' and the cardiac structure will move in synchrony with each other when the catheter 12' and coupling device is aligned and anchored to the heart.

In another example of the system 1, the angled side port is angled towards the coupling device. By angling the side port in a direction towards the coupling device the interventional device, will hit the coupling device with a high accuracy and ease and the coupling device may in turn direct the interventional device, further to deploy and/or retrieve the interventional device, not easily reached from the catheter 12' due to an obstruction in a direct path to the target site. Alternatively, it is easier to steer the interventional device, at the coupling device when the anatomical structure of interest is in contact with the coupling device. In yet another example, the angled side port is angled such that the target point A is reached based on the shape of the interventional device, that is used for the deployment and/or retrieval. By adapting the angle of the angled side port to the shape of the interventional device, used for the deployment and/or retrieval it is possible to hit a specific target point A without altering a preferred shape of the interventional device. This allows for devices to be used "out of the box" together with the steering system by a simple adaptation of the side port instead of the interventional device.

In one example the catheter 12' comprises at least two lumens. By having at least two lumens it is possible to in an easy way guide the interventional device, in a vicinity of the angled side port when moved inside the catheter 12' within one of the lumens, allowing for easier deployment and/or retrieval of the interventional device, from the interior to the exterior of the catheter 12', or vice versa.

One example of an even easier way of guiding the interventional device, to the side port, is that the distal end of the catheter 12' is connected to one of the at least two lumens and wherein the angled side port is connected to an end of the other of the at least two lumens. By having the end of one of the at least two lumens connected to the angled side port it is possible to in a very easy way guide the device to the angled side port since the lumen will be bend or otherwise configured to end at the angled side port so that the device will follow the path of the lumen to reach the angled side port.

In one example, the interventional device, that is deployed and/or retrieved through the angled side port is an annuloplasty implant 200. By using the side port 4, 4', it is easy to deploy an annuloplasty implant in the heart since the direction of the angled side port is known and the shape of the annuloplasty implant is known and which combined makes it possible to hit the target point A of interest for deploying the annuloplasty implant. In another example, as described above, the coupling device is first targeted and then used for directing the annuloplasty implant 200 through the commissure 11 or commissures into place at mitral valves 11', see FIG. 7c. In the example shown in FIG. 7c the annuloplasty implant 200 is a helix ring with a lower ring 200 positioned below the valve in the ventricle, and an upper ring 201 positioned in the atrium, trapping the valve tissue therebetween.

In one example the coupling device is extendable from the interior of the catheter 12' to the exterior of the catheter 12 at the distal end of the catheter 12'. By having the coupling device extendable, i.e. collapsible and expandable, from the catheter 12' it is possible to adjust the relation between the coupling device and the catheter 12' for even a more versatile steering system. It also achieves an easy construction of the steering system were the coupling device may be deployed after the catheter 12' and manipulated by an operator firstly to achieve the anchoring and alignment of the coupling device and then looking the catheter 12' in place, secondly. Such locking mechanisms may be any kind of protrusions on the coupling device inside the catheter 12' or outside the catheter 12' for engagement with a corresponding ingrowth on the catheter 12' so that the two are locked when engaged.

In one example, the coupling member of the coupling device comprises an extensible wire 3' that is deployed radially outward to engage the cardiac structure, see FIG. 7d. By using an extensible wire as the coupling member an easy but still rigid and secure coupling device is achieved.

In another example, the coupling member comprises at least one radially expansible superior loop and at least one radially expansible inferior loop, wherein the superior loop contacts a superior surface at the cardiac structure and the inferior loop contacts an inferior surface at the cardiac structure when the loops are in an expanded position to capture a portion of the cardiac structure between the loops, such as with the commissure locator 30. By having the coupling member being shaped like an "hour-glass" it is possible to have an easy but yet effective coupling member that conforms to the shape of the cardiac structure such as the commissures for anchoring and alignment of the catheter 12' and coupling device. Other types of coupling members are also used that are more suitable to other shapes of cardiac structures such as stents, cages, snares, screws and so on.

According to another example of the invention a method for deploying and/or retrieving at least one interventional heart device, used in heart procedures wherein the method comprises a step of introducing a catheter 12 into a heart adjacent to a cardiac valve, wherein the catheter 12' has a distal end and a proximal end. A further step of placing a coupling device arranged at the distal end of the catheter 12', comprising a coupling member configured to engage at least one pre-determined cardiac structure for coupling and aligning the catheter 12' in a known direction in the heart. And even further a step of retrieving and/or deploying the at least one interventional heart device, through the at least one angled side port on the catheter 12', wherein the angled side port is between the proximal end and the distal end of the catheter 12'. By using the method as described above for aligning and anchoring the catheter 12' and the coupling device an easy, quick and reliable way of deploying and/or retrieving the interventional device, is achieved.

In one example the retrieving and/or deploying is performed by a second catheter 12' through the at least one angled side port of the catheter 12'. By using the second catheter 12' a straight path is used for hitting the desired target point A.

Various ways of entering the heart is possible with the steering system and the introducing of the catheter 12' into the heart may be performed transseptal, transaortic and/or transapical.

FIG. 7 also illustrates the coronary sinus contractor 20 of the system 1, used in conjunction with the commissure locator device 30. The synergetic advantages of the aforementioned components of system 1 have been described above. The components of the coronary sinus contractor 20 is described in more detail below.

Figure 11:
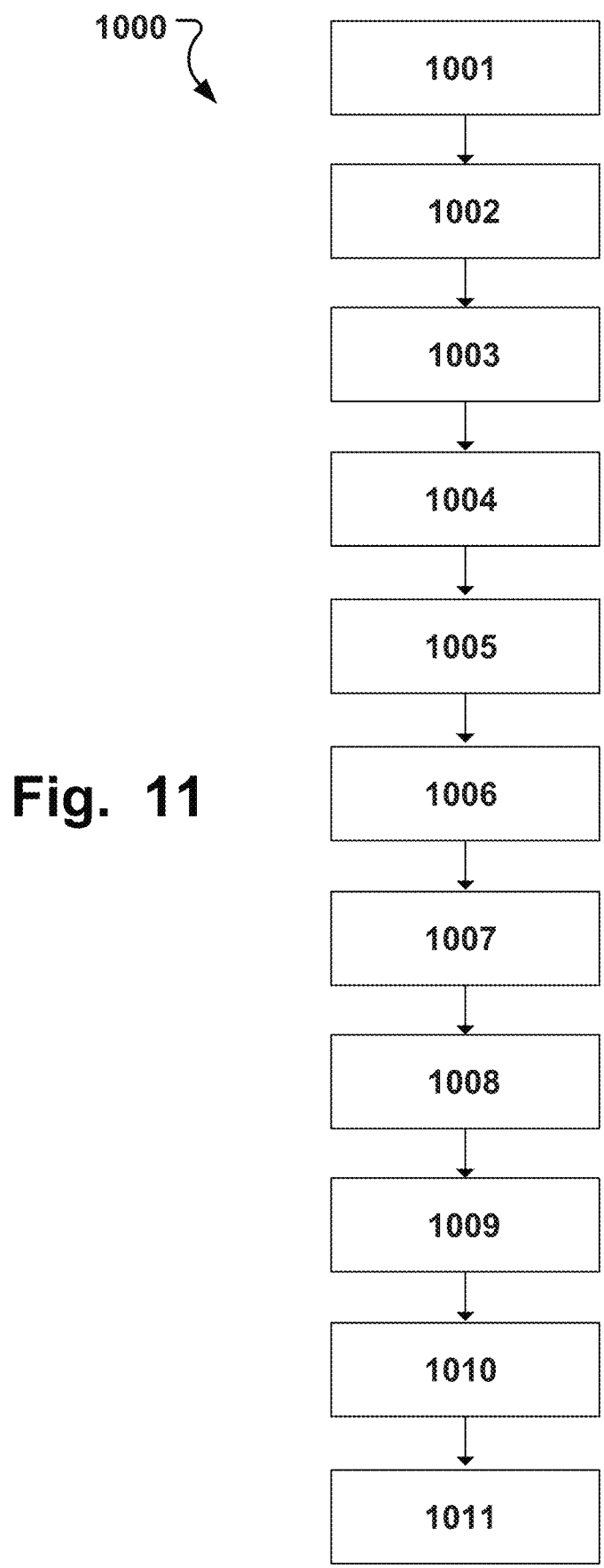
FIG. 11 is a flowchart of a method of using a delivery system for delivery of an annuloplasty implant.

In one example a complete procedure for performing an annuloplasty procedure in accordance with the above disclosure comprises the steps of, with no limitation in the order in which the steps are carried out: introducing through a femoral vein a septal wall device to a septal wall; puncturing the septal wall with the septal wall device allowing access to the left atrium; introducing a coronary sinus contracting device for forming the mitral valve annulus; forming the mitral valve annulus with the coronary sinus contracting device; inserting of a commissure locator and expander device, or the steering system described above through the septal wall puncture; deploying a helix ring in left atrium; maneuvering the helix ring into position through a posterior commissure placement; fastening the helix ring in a perpendicular direction to a mitral annulus; and removing of devices, leaving the helix ring securely in place. By using the above described method of deploying an annuloplasty implant, a quick, easy and reliable way is achieved. The method 1000 is further described with reference to FIG. 11.

Coronary Sinus Contractor

The coronary sinus (CS) lies adjacent the mitral valve (MV) and follows a curvature around the annulus (A) of the MV.

Figure 5A:
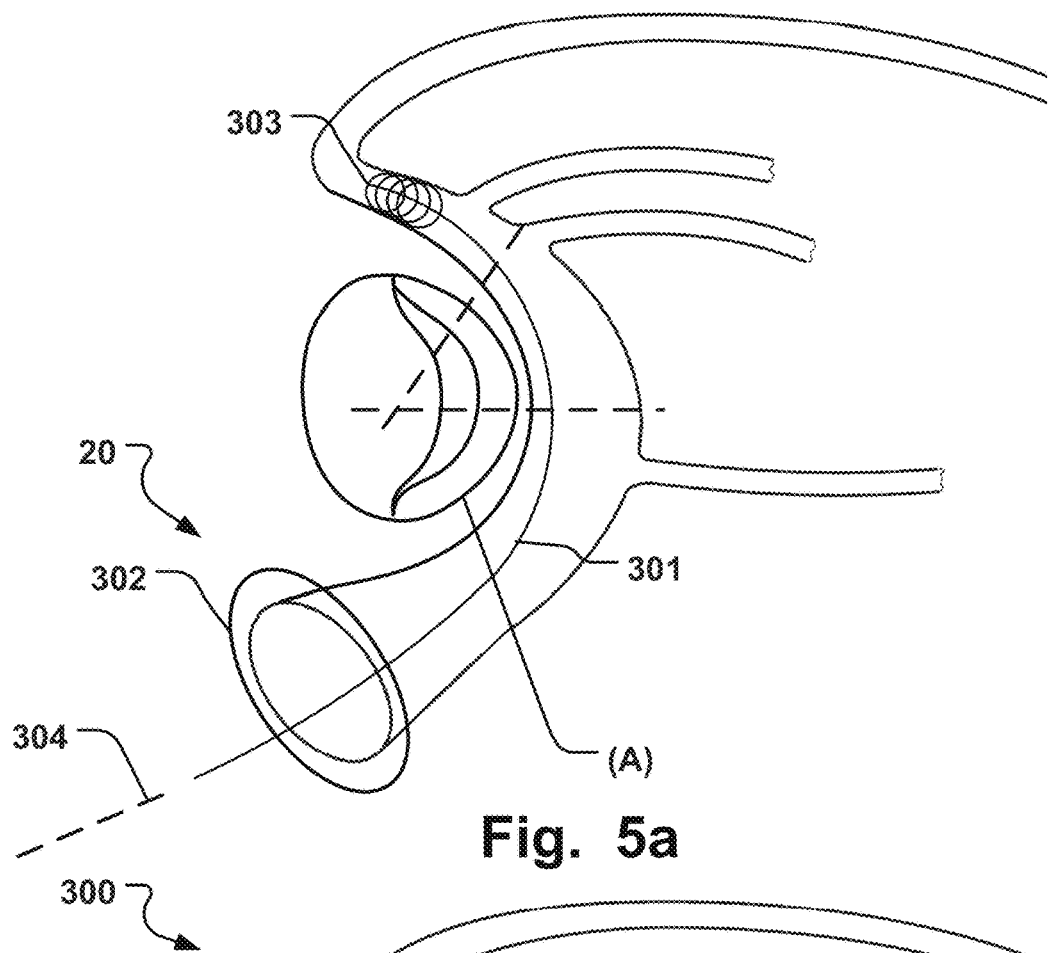
FIG. 5a is a view of an example of a coronary sinus contractor of a delivery system for delivery of an annuloplasty implant in a delivery state.
Figure 5B:
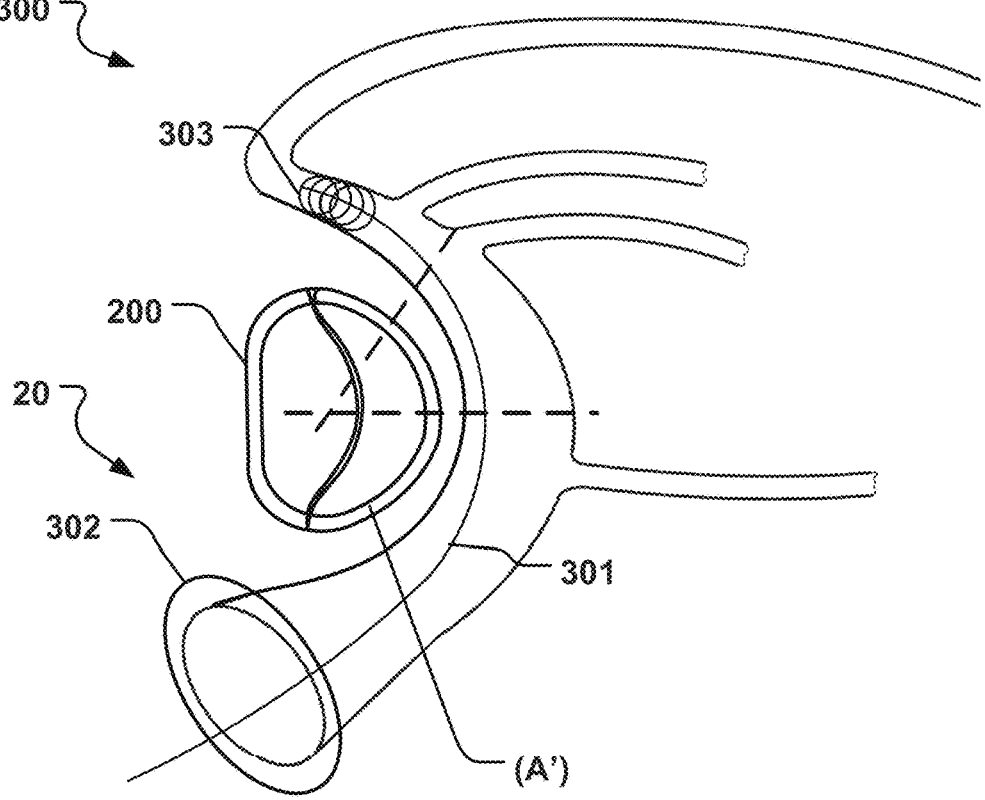
FIG. 5b is a view of an example of a coronary sinus contractor of a delivery system for delivery of an annuloplasty implant in an activated state.
Figure 6A:
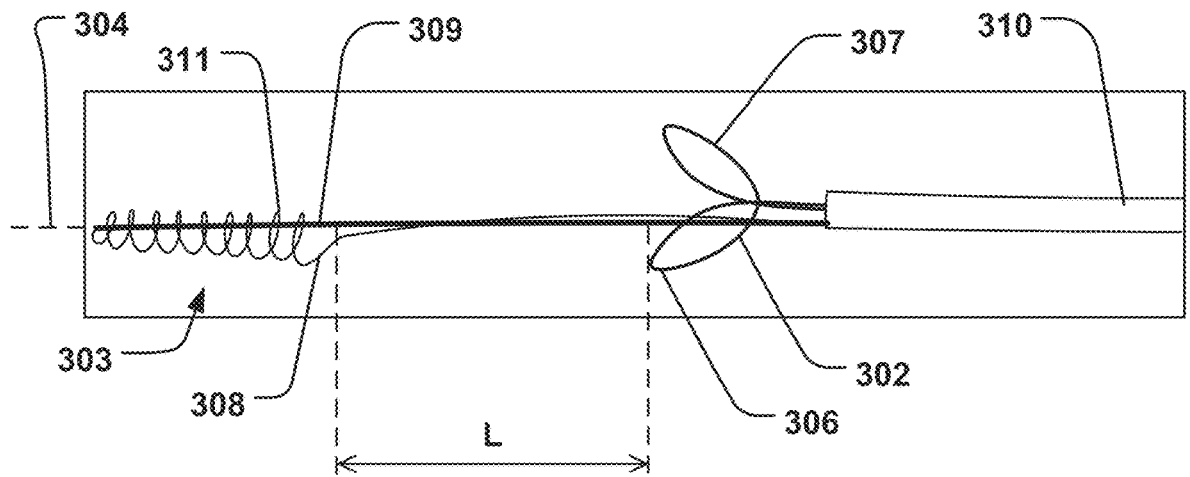
FIG. 6a is a view of an example of a coronary sinus contractor of a delivery system for delivery of an annuloplasty implant in a delivery state.
Figure 6B:
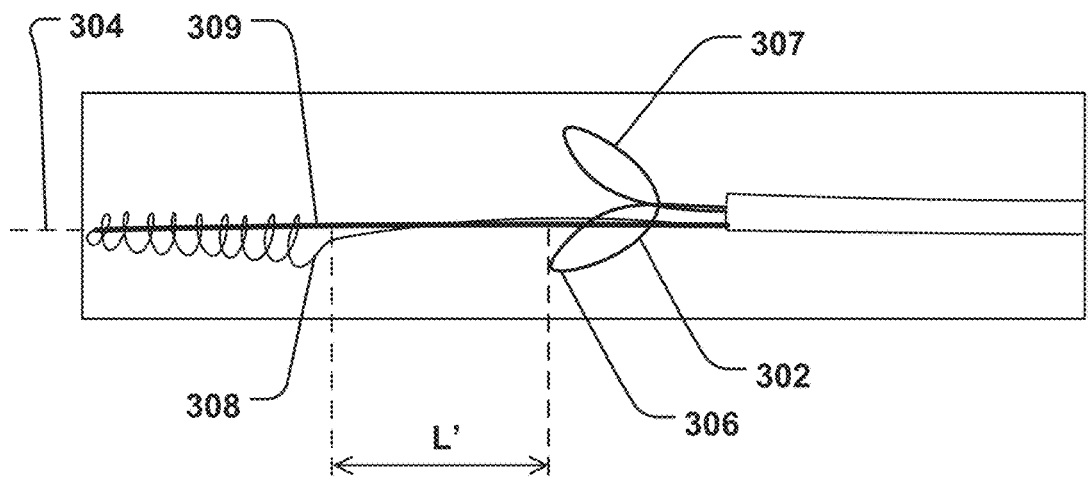
FIG. 6b is a view of an example of a coronary sinus contractor of a delivery system for delivery of an annuloplasty implant in an activated state.

The coronary sinus contractor 20, FIGS. 2, 36, comprises displacement unit 301 for temporary insertion into a coronary sinus (CS) adjacent the valve, wherein the displacement unit has a delivery state (FIG. 5a) for delivery into said CS, and an activated state to which the displacement unit is temporarily and reversibly transferable from the delivery state. The displacement unit comprises a proximal reversibly expandable portion 302, a distal anchoring portion 303 being movable in relation to the proximal expandable portion in a longitudinal direction 304 of the displacement unit (so that the distance (L) between the two portions 302, 303, is reduced as seen in FIGS. 6a-b) to the activated state in which the shape of the annulus is modified to a modified shape (A') (FIG. 5b); and an annuloplasty device 102 for permanent fixation at the mitral valve annulus by annuloplasty of the valve when the modified shape is obtained (FIG. 5b). The annuloplasty device 102 comprises a fixation structure 103 that is adapted to retain the modified shape. By moving the distal anchoring portion 303 in the longitudinal direction towards the proximal expandable portion 302 the radius of curvature of the CS and also the valve annulus can be reduced. The modified shape of the annulus is then fixated by the annuloplasty device 102, before removing the displacement unit 101. Previous prior art devices for insertion into the CS are for permanent implantation and are not adapted to be removed or used in conjunction with an annuloplasty device 102. Alternatively, the prior art devices are focused bending of a segmented device only. The combination of reducing the length of the displacement unit 301 and having a proximal expandable portion 302 that efficiently provides a counter force against the anchoring portion 303, greatly improves the downsizing effect. Absence of a proximal expandable portion will make the downsizing considerably more difficult. The system 300 allows for improved efficiency treating diseased valves due to efficient downsizing of the valve via the CS and subsequent fixation of the annulus at the valve itself. Both the proximal expandable portion 302 and the distal anchoring portion 303 are reversibly expandable for delivery and retrieval from a sheath 310, see FIG. 6a. In one embodiment the distal anchoring portion 303 and/or the proximal expandable portion 302 may pivot towards the longitudinal direction 304 in order to be easily retracted into the sheath 310, see FIG. 2. The distal anchor is inserted and fixated into the CS and the proximal reversibly expandable portion 302 folds out from the sheath 310 to allow for performing the downsizing and is then folded back into the sheath 310 and is retracted.

The implant 200 is adapted to retain the modified shape of the annulus in the delivery state of the displacement unit after temporary activation in the activated state. The implant 200 may be a helix ring that pinches the tissue of the leaflets, and fixation of the helix is may also be done by the stapling device 40, to retain the modified shape.

The distance (L) between the proximal expandable portion 302 and the distal anchoring portion 303 in the longitudinal direction 304 decreases to a reduced distance (L') when the displacement unit 301 is transferred from the delivery state to the activated state, see FIGS. 6a-b. Since the distal anchoring portion 303 is fixated in the CS decreasing the distance between the proximal expandable portion 302 and the distal anchoring portion 303 will result in a reduced radius of curvature of the CS which will downsize the valve. Thus, the radius of curvature of the displacement unit 301 decreases when the displacement unit is transferred from the delivery state to the activated state.

Figure 4:
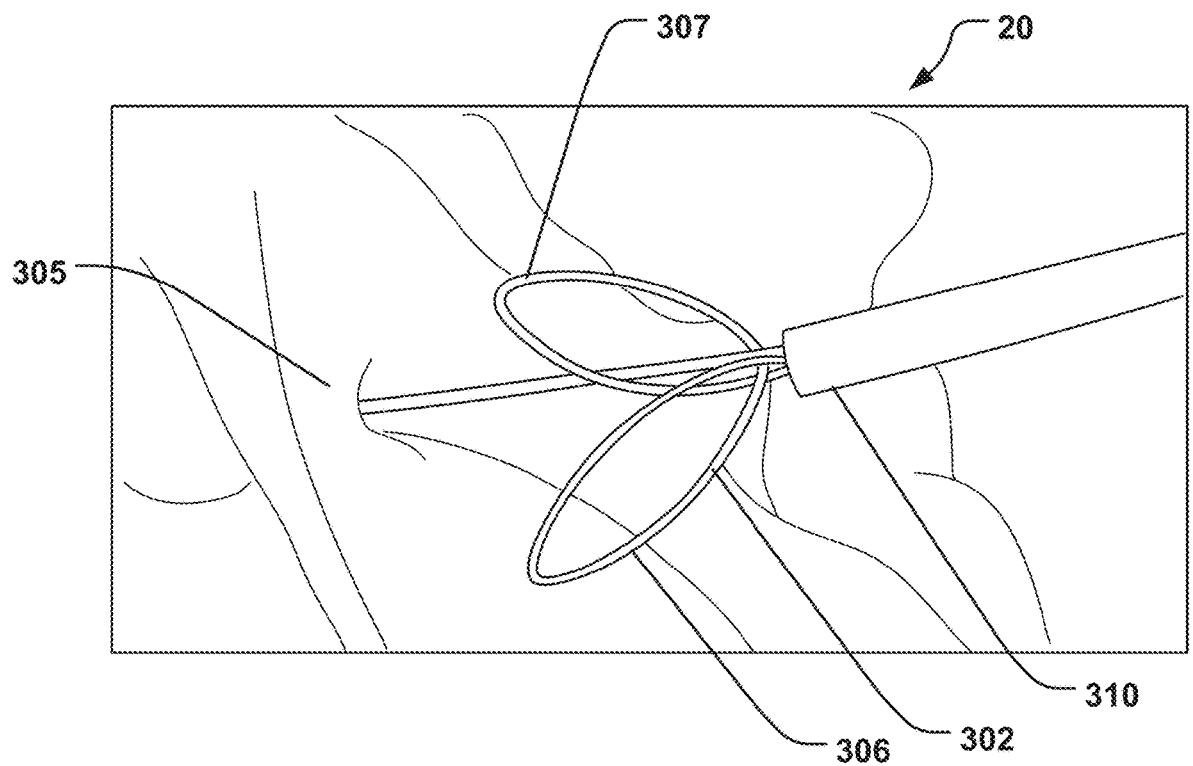
FIG. 4 is a view of an example of a coronary sinus contractor of a delivery system for delivery of an annuloplasty implant.

The proximal expandable portion 302 may be reversibly foldable to an expanded state for positioning against a tissue wall 305 at the entrance of the CS, as shown in FIG. 4. This provides for a very stable fixation of the position of the proximal expandable portion 302 relative the distal anchor 303 for improved control of the downsizing of the valve. Since the proximal expandable portion 302 may be shaped and adapted for positioning against the tissue wall 305 at the entrance of the CS, and not inside the CS itself it also reduces the risk of damaging the CS. Also, since the proximal expandable portion 302 is positioned outside the CS it is not constrained by the size of the CS and can thus be reversibly expanded to a diameter that spreads the force over a larger portion, thus reducing the pressure on the tissue. This also reduces risk of damages.

The proximal expandable portion 302 may comprise expandable wire lobes 306, 307, for positioning against the tissue wall 305 at the entrance of the CS, see FIG. 4. The wires lobes are adapted to be fixated against the tissue wall outside the CS, and provide for a stable fixation point. The wire lobes 306, 307 may expand on either side of the sheath 310 to spread the force symmetrically for controlled positioning. Any expandable structure such as a balloon etc. may be provided as proximal expandable portion 302 for reversible expansion against the tissue wall 305 at the entrance of the CS, i.e. outside the C8 to provide the above mentioned advantages.

The proximal expandable portion 302 may have a larger expanded diameter than the distal anchoring portion 303 in the activated state of the displacement unit 301. This is e.g. illustrated in FIG. 3, and allows the proximal expandable portion 302 to be more securely positioned in relation to the anchor 303 for a more controlled downsizing.

The distal anchoring portion 303 is expandable to anchor against said CS in the activated state of the displacement unit 301. It provides sufficient force against the C8 to be fixated relative the proximal expandable portion 302 when pulling the distal anchoring portion 303 towards the proximal expandable portion 302.

The distal anchoring portion 303 may comprise an expandable coiled wire 311, see FIG. 3. The coiled wire provides for efficient fixation against the CS, since pressure is provided evenly and circumferentially along the length of the coil, while at the same times allows to be easily retracted into the sheath 310 by extending the coil in the longitudinal direction 304. The coiled wire may be connected to a control wire 308, FIG. 3, which is adapted to stretch the distal anchoring portion to a reduced diameter delivery shape, and reduce tension on the coiled wire in the activated state to expand the distal anchoring portion. Hence, it also allows for easy deployment of the distal anchor in the C8 by reducing the tension on the coil so that it can be retracted and expanded in diameter for fixation against the CS. Further, the coil 311 provides for keeping the body lumen open so that blood flow can be maintained.

The displacement unit 301 may comprise a delivery wire 309, FIGS. 3 and 6a-b, adapted to deliver the distal anchoring portion 303 and to pull the distal anchoring portion 303 towards the proximal expandable portion 302 in the activated state, whereby the distance (L) between the two is reduced to the shorter distance (L'), as illustrated in FIGS. 18a-b, to provide the downsizing. The control wire 308 for the anchoring portion 303 may be pulled simultaneously and with the same displacement so that the anchoring portion maintains its length in the longitudinal direction 304.

The proximal expandable portion 303 may be reversibly foldable to an expanded state where the proximal expandable portion 303 has a diameter substantially larger than the diameter of the CS. This allows for a more stable fixation outside the CS with the advantages mentioned above.

The anchoring portion may comprise a tissue retention portion such as at least one hook (not shown). The tissue retention portion provides for efficient fixation of the anchoring portion 303 inside the CS, that allow for efficient downsizing of the valve annulus. Any number of retention portions can be used, to optimize the efficiency of the procedure. In addition to hooks, other retention members grasping the tissue can be provided. The retention portions are preferably oriented towards the myocardial wall of the CS which is more robust for grasping of the retention portions.

The anchoring portion 303 may comprise a tissue apposition portion (not shown) having a tissue atraumatic surface, such as an at least partly curved or spherical surface. The tissue apposition portion provides for exerting a counter force against the wall of the CS, stabilizing the anchoring portion 303, and allowing for the retention portion to more efficiently grasp the tissue and anchor against the same. Also, it helps keeping the CS vein open for sustaining a flow of blood, in addition to the coil 311 which also keeps the CS vein open. By having a tissue atraumatic surface, the tissue apposition portion enhance the anchoring ability while at the same time reducing the risk of tissue damage to the wall of the CS.

The tissue retention portion may be expandable in a direction substantially perpendicular to the longitudinal direction 304. It may therefore efficiently engage the wall of the CS. For example, the retention portion can be formed of a metal alloy having a heat set shape where it assumes an outwardly curved shape, for engaging the tissue. The retention portion may be connected to the delivery wire 309, such that when the delivery wire is pulled back relative the proximal expandable portion 302, the retention portion grasp the tissue, anchors the anchoring portion 303, and draw the tissue against the proximal expandable portion 302 to achieve the reduced length (L') and the downsizing effect. Alternatively, or in addition, the retention portion may be connected to a separate control wire (not shown) so that the radially outward expansion of the retention portion can be controlled independently of the position of the delivery wire 309. Thus, the retention portion may first be retracted, e.g. within the coil 311, before pushed in the longitudinal direction 304, where it may assume the heat set radially expanded shape for grasping the tissue as discussed.

The tissue apposition portion may be controlled and deployed in the same manner as described in the preceding paragraph for the retention portion, e.g. being connected to delivery wire 309 or a separate control wire (not shown), such that the tissue apposition portion can be expandable in a direction substantially perpendicular to the longitudinal direction 304 for contacting the all of the CS.

The tissue retention portion and said tissue apposition portion may be expandable in substantially opposite directions. This allows the tissue apposition portion to provide a good counter force relative the retention portion for efficient grasping of the tissue and secure anchoring. Also, while the retention portion is directed to the stronger myocardial wall, the tissue apposition portion 313 is placed against the more sensitive side of the CS.

The displacement unit may comprise, at a radial portion thereof, at least one radiopaque marker for rotational alignment of the displacement unit in the CS. E.g. the tissue apposition portion may have a radiopaque marker for assisting in orienting away from the myocardial wall. Alternatively, or in addition the retention portion may comprise a radiopaque marker 109.

A method for treating a defective mitral valve (V) having an annulus (A) is disclosed comprising; inserting a flexible and removable elongate displacement unit 301 in a delivery state into a coronary sinus (CS) adjacent the valve, positioning a proximal expandable portion 302 against a tissue wall 305 at the entrance of the CS, positioning a distal anchoring portion 303 inside the CS, activating the displacement unit in an activated state whereby the distal anchoring portion is moved in a longitudinal direction 304 of the displacement unit to reduce the distance between the distal anchoring portion and the proximal expandable portion such that the shape of the annulus is modified to a modified shape (A'), fixating an annuloplasty device 102 at the mitral valve annulus when the modified shape is obtained, whereby the annuloplasty device comprises a fixation structure 103 that is adapted to retain the modified shape, removing the elongate displacement unit after temporary activation in the activated state.

Stapling Device

The stapling device 40 for fixating the implant 200 to tissue with a clip 205 is shown in FIG. 10. The stapling device comprises a sheath 401 having a distal end 402 for delivery of the clip, and a pusher unit 403, 403', being movable inside the sheath along a longitudinal direction 404 of the sheath. The distal end comprises a clip guide 405, 405', in which the clip is movable in the longitudinal direction. The clip guide has a closed configuration in which the clip guide is adapted to apply a restraining force on the clip so that the clip assumes a delivery shape. The closed configuration of the clip guide 405, 405'. The clip guide 405, 405' also has an open configuration in which the clip 205 assumes a relaxed shape. The pusher unit 403, 403', is movable from a proximal position (P) in which the clip guide is in the closed configuration, to a distal position in which the pusher unit 403, 403', engages the clip guide 405, 405', and the clip guide is in the open configuration.

By a single step movement, of the pusher 403, 403', from the proximal position to the distal position the clip 205 is transferred from the delivery shape to the relaxed shape. If the clip 205 is inserted into the tissue in the delivery shape it can thus be conveniently and quickly transferred to towards the relaxed shape, in which it may clamp the tissue and fixate the position of e.g. an implant such an annuloplasty implant. The single step movement also provides for a simple and inexpensive device to manufacture, which also can be made as a single-use disposable device. The clip 205 may be preloaded into the sheath 401. Since the clip 205 has its delivery shape already when the pusher 403, 403', is in the proximal position there is no additional action needed to engage the clip 205 to transfer it into the delivery shape. This also allows for achieving improved stability in the longitudinal direction 404 as explained below when the clip 205 is in the delivery shape, and allowing for further guiding in the longitudinal direction 404 when the pusher is engaged to the distal position.

Thus, by having a clip guide 405, 405', in which the clip 205 is movable in the longitudinal direction 404 of the sheath, while being transferred from the closed to the open configuration, the position of the clip in the longitudinal direction 404 can be ensured to thereby attain high stability and accuracy when positioning of the clip 205 in the delivery shape until the clip is fixated in the relaxed shape. For example, when the pusher 403' moves from the proximal position (P) to the distal position (P'), the clip 205 moves in the longitudinal 404 direction in the clip guide 405, 405'. In the proximal position of the pusher, when the clip 205 is restrained to assumes its delivery shape, the clip 205 can be positioned in the tissue due to the legs 200, 200' extending well outside the clip guide 405, 405. In this configuration, the clip guide holds the clip securely, since it functions as a guide in the longitudinal direction, so that the clip can be inserted into tissue without tilting or otherwise dislocate relative the longitudinal axis 404. As the pusher 403' moves to the distal position the clip guides 405, 405', guides the clip 205 in the longitudinal direction, maintaining a stable delivery path, while the clip assumes the relaxed shape. The stable delivery path in the longitudinal direction 404 make sure that there is no uncertainty in the position of the clip relative the sheath, crucial e.g. when operating in difficult conditions. The relaxed shape of the clip 205 may be determined by heat treatment procedure, and the clip may be formed of a nitinol or another suitable material for heatsetting. The clip 205 may not fully assume its relaxed shape when inserted into tissue due to the counter force exerted from the tissue on the clip, but the clip will strive to the relaxed shape which results in a compressive force between the clip and tissue.

The clip guide 405, 405', may comprise a clip track 406, 406', being arranged to partly enclose a leg 200, 200', of the clip 205 and apply the restraining force previously mentioned and thereby align the clip in the longitudinal direction 404 when the clip guide is in the closed configuration. Hence, when the clip is in the delivery shape, the clip track 406, 406', of the clip guide may force the leg, or legs 200, 200', of the clip 205 into a certain position such as in the longitudinal direction. The clip tracks 406, 406, may thus also be aligned in this direction. However, it is conceivable that the clip tracks 406, 406', may have an angle relative the longitudinal axis 404 in certain applications in order to be able to deliver the clip in a certain angle relative the sheath. By having a clip track 406, 406, an improved alignment of the clip can be provided so that it follows a desired path when being transferred from the delivery shape in which the legs are restrained, to the relaxed shape. Upon moving the pusher 403' to the distal position, and transferring the clip to the relaxed shape, the clip tracks 406, 406', may continue to steer the legs 200, 200', of the clip 205 in the desired path, even if the clip tracks 406, 406', do not fully enclose the legs 200, 200', of the clip 205. The pusher 403' may be shaped to pass through, between or at the side the clip tracks 406, 406', while latter still provide guiding of the clip along the desired path.

The clip guide 405, 405', may comprise two guide parts 407, 408, 407', 408', being separable in opposite directions B, B' and in directions perpendicular to the longitudinal direction 404. The separation of the two guide parts 407, 408, 407', 408', removes the restraining force on the clip so that the clip can assume its relaxed shape. This provides for particularly improved functionality for transferring the clip 205 from the delivery shape to the relaxed shape. For example, by having two guide parts 407, 408, of the clip guide 405 that are separable in opposite directions, the force and also the range of movement required to release the restraining force on the clip may me reduced since each of the guide parts has to travel a smaller distance when being moved from the closed to the open configuration. The symmetric action also reduce the risk of undesired displacement in a particular direction transverse to the longitudinal axis 404 when the restraining force on the clip is released.

The pusher unit 403' may in its distal position G' separate the two guide parts 407, 408, 407', 408' in the mentioned opposite directions B, B', whereby the clip guide 405, 405', assume its open configuration. This allows for simultaneously moving the clip 205 along the longitudinal axis 404 with the pusher, i.e. further into the tissue at the target site, and moving the clip guide from the closed to the open configuration so that the clip can assume the relaxed shape to clamp the tissue, and/or securely attach an implant to the tissue. Attaching a clip 205 and fixating tissue and implant in such single step movement provides for a quicker and easier procedure. The force acting on the pusher 403' both drive the clip forward and transfers the clip from the delivery shape to the relaxed shape in a continuous motion. In contrast to prior art, there is accordingly no need to first apply a force onto the clip with a pusher in order to transfer the clip from a relaxed shape to a delivery shape, insert the clip, and then apply a second force in a different direction to the device in order to release the clip to the relaxed configuration while the pusher is already acting on the clip with the first force. The latter example implies a more complicated device that also results in that the total force applied on the stapling device is increased, e.g. both due to the added second force, and due to that the second force must be sufficiently large to overcome the first force acting on the clip, since the forces are counteracting. This leads to an increase in frictional force against the clip, and such counteracting forces that the operator must apply to the device makes handling less precise. Sensibility to movements e.g. of the surrounding anatomy is decreased in such previous devices. This is resolved with the single-step movement with a pusher force that acts to achieve the two functions as described above.

The two guide parts 407, 408, 407', 408' may be separable in directions B, B' along a tangent line 409 to the sheath 401. This allows for maintaining a compact profile of the sheath 401 even when the clip guide 405, 405', is in the open position, since the movement is contained as close to the periphery of the sheath 401 as possible.

The two guide parts 407, 408, 407', 408' may each comprise a clip track 406, 406', arranged on either side of a leg 200, 200', of the clip 205 to apply the mentioned restraining force and align the clip 205 in the longitudinal direction 404 when the clip guide 405, 405', is in the closed configuration. By retaining the clip on each side of the leg in a clip track the precision in the alignment of the clip is improved, since it is possible for the two guide parts to partly enclose the clip on either side of the leg.

The clip guide 405, 405', may be resiliently movable from the closed configuration to the open configuration. This provides for a smooth and predictable resistance acting on the movement of the pusher 403' when engaging the clip guide. This allows for a controlled action when moving the clip from the delivery shape to the relaxed shape and a controlled release. The stapling device 40 may comprise a resilient unit 410 arranged to apply the resilient force on the clip guide 405, 405'. The resilient unit 410 may be provided at the periphery of the sheath 401 and contacting the clip guide 405, 405', to counteract movement thereof with a predefined resistance that can be adjusted by varying the resilience or flexibility of the resilient unit 410. The resilient unit 110 may be provided radially outside the clip guide 405, 405', to apply a counteracting force radially inwards. The resilient unit 410 may be a ring of flexible material such as silicone or other flexible polymer, or wires of a flexible alloy or fabric.

The pusher unit 403 may comprise a distal tongue 403' arranged to push the clip 205 through the clip guide 405, 405', in the longitudinal direction 404 and move the clip guide 405, 405', from the closed configuration to the open configuration. Hence, it provides for moving the clip 205 along the longitudinal axis 404 with the pusher and simultaneously moving the clip guide from the closed to the open configuration so that the clip can fixated in the relaxed shape. A narrow distal tongue 403' allows for a compact design of the clip guide even in the open configuration, and the tongue 403' will only displace the clip guide a small distance relative the diameter of the sheath 401 to maintain a compact profile.

The distal tongue 403' may engage an angled surface 412 of the clip guide 405, 405', relative the longitudinal direction 404 when the pusher unit 403' is moved from the proximal position to the distal position, so that the clip guide is moved from the closed configuration to the open configuration. The angled surface 412 allows the tongue 403' to easily slide into the correct position and move through the clip guide 405, 405', which improves precision of the and device 40. It also provides for a more gradual transition from the closed to the open configuration as the angled surface 412 slides against the pusher 403' with gradual displacement in the radial direction. The clip 205 can thus be moved from the delivery shape to the relaxed shape more gradually as it advances along the longitudinal axis 404. This may be desired in certain situations where it is desired to delay the movement of the clip 205 to the relaxed shape.

The distal tongue 403' may be arranged for engagement with the clip 205 at an engagement surface having a recess to receive a portion of the clip 205. This provides for increasing the radial stability of the clip as the recess prevents movement in the radial direction.

The clip guide 405, 405', may comprise a first 405 and a second 405' clip guide arranged at radially opposite peripheries of the sheath 401 and extending in the longitudinal direction 404. This is illustrated in the exemplary embodiment of FIG. 10, and allows for improved accuracy in guiding the clip 205 when moving the clip forward by ensuring guiding at both sides of the clip being positioned radially across the sheath 401. Tilting or other dislocation of the clip is prevented. The first and second clip guides 405, 405', may be being arranged to partly enclose a first 200 and a second 200' leg of the clip, respectively, and align the clip in the longitudinal direction 404 when the clip guide is in the closed configuration. This further improves the positioning of the clip at the peripheries of the sheath 401. Each of the first and second clip guides 405, 405', may comprise two separable guide parts 407, 408, 407', 408' as illustrated in FIG. 10.

The pusher unit 403' may simultaneously engage the first and second clip guides 405, 405', when moved from the proximal position to the distal position, whereby the two separable guide parts 407, 408, 407', 408' of each of the first and second clip guides are separated to assume the open configuration. This provides for stabilizing both legs 200, 200', of the clip to simultaneously as the clip is pushed through the clip guide.

Stapling kit according to one embodiment is disclosed, comprising a stapling device 401 as described above and a clip 205 having legs 200, 200'. The clip 205 has a delivery shape in which the legs are substantially parallel, and a relaxed shape wherein the legs cross each other. The crossed legs allows for increasing the strength of the fixation of an implant such as an annuloplasty ring to tissue, and preventing dislocation by locking the implant in place.

The clip 205 may be adapted to form a loop around a first and second ring of a helix-shaped implant positioned on either side of heart valve tissue.

A method of releasing a clip from a stapling device 40 is disclosed comprising providing a pre-loaded clip in the stapling device 40 having a sheath and a clip guide at a distal end of the sheath; moving a pusher unit inside the sheath from a proximal position to a distal position to engage the clip guide in which the clip is movable in a longitudinal direction of the sheath. Moving the pusher to the distal position comprises moving the clip guide from a closed configuration, in which the clip guide is adapted to apply a restraining force on the clip so that the clip assumes a delivery shape, to an open configuration in which the clip assumes a relaxed shape, whereby when the clip is in the relaxed shape the clip is released from the stapling device 40.

A method is disclosed of delivering a clip to a target site from a stapling device 40 as described above. The method comprises providing a pre-loaded clip in the stapling device 40 having a sheath and a clip guide, at a distal end of the sheath; navigating the sheath to the target site such as a heart valve; attaching a part of the clip to the target site for fixating tissue and/or fixating an implant, such as an annuloplasty ring to tissue; moving a pusher unit inside the sheath from a proximal position to a distal position to engage the clip guide. Moving the pusher to the distal position comprises moving the clip guide from a closed configuration, in which the clip guide is adapted to apply a restraining force on the clip so that the clip assumes a delivery shape for attaching said part of the clip, to an open configuration in which the clip strives towards a relaxed shape where legs of the clip has a crossed configuration. Moving the clip guide comprises attaching a remaining part of the clip to the target site, and whereby when the remaining part of the clip is attached to the target site, the clip strives to the relaxed shape and applies a compressive force to the tissue and/or implant for fixating the tissue and/or implant, and releasing the clip from the stapling device 40.

When said remaining part of the clip is attached to the tissue, legs of the clip may form a loop around a first and second ring of a helix-shaped implant positioned on either side of heart valve tissue.

Method

Illustrated in FIG. 4 is an example of a method 1000 of implanting an annuloplasty implant, with a system disclosed above. First, a puncture and/or cannulation of the femoral vein is performed.

Following, is an insertion of a septal wall device such as a Mullins Introducer Sheath and/or a Brockenbrough Needle performed.

Then, the commissure locator and expander device is moved into place 1001 by use of the septal wall device, in order to find the commissures in the heart and support the heart during the rest of the procedure. In an example, the delivery sheath will be withdrawn when device is in position, allowing the nitinol wire to spring back to a preformed shape and expanding the commissures to a full extension.

The coronary sinus contracting device, i.e. displacement unit 301, is deployed 1002, such as via the jugular vein. The coronary sinus contractor 20 device will ensure the approximation of the mitral annulus towards anterior leaflet for the placement of the helix ring. In an example the sinus contractor device will be used in parallel with the commissure stabilizing device, and/or the coronary sinus contractor 20 is positioned in the CS before the commissure locator is positioned at the commissures.

The displacement unit is activated (1003) in an activated state whereby the shape of the annulus is modified to a modified shape (A').

Then, a stepwise deployment of the annuloplasty ring 1004, such as a helix ring, via the left atrium is performed. The ring is deployed into position through a posterior commissure placement by use of the implant delivery and retractable device 30.

Following, the operator fastens the ring 1005 perpendicular to the mitral annulus by using the stapling device 40 to retain the modified shape (A').

Finally, the devices, including the displacement unit, are removed 1006, leaving the ring securely in place at the mitral valve.

Activating the displacement unit in an activated state may comprise positioning 1007 a proximal expandable portion 302 against a tissue wall 305 at the entrance of the CS, positioning 1008 a distal anchoring portion 303 inside the CS, activating 1009 the displacement unit in an activated state whereby the distal anchoring portion is moved in a longitudinal direction 304 of the displacement unit to reduce the distance between the distal anchoring portion and the proximal expandable portion such that the shape of the annulus is modified to said modified shape (A'). This provides for efficient downsizing of the annulus.

Inserting said implant around the annulus of the heart valve may comprise guiding 1010 said implant into place by guiding means positioned at the commissure locator device at a portion to be arranged at the commissures. This makes the positioning of the implant easier.

The method 1000 may comprise measuring 1011 the distance between the commissures by said commissure locator device for receive a measure for determining a size of the implant to be inserted. Thus the correct size of the implant can thus be advantageously determined simultaneously during the procedure.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

What is claimed is:

1. A method of delivering an annuloplasty implant comprising,
   inserting a flexible and removable elongate displacement unit in a delivery state in the coronary sinus (CS) adjacent a heart valve,
   activating the displacement unit in an activated state whereby the shape of the annulus of the heart valve is modified to a modified shape,
   introducing a catheter at the heart valve to deliver the annuloplasty implant,
   inserting the annuloplasty implant around the annulus of the heart valve,
   fixating the annuloplasty implant at the annulus when the modified shape is obtained,
   removing the elongate displacement unit after temporary activation in said activated state.

2. Method according to claim 1, wherein the annuloplasty implant comprises a helix ring, wherein the helix ring is placed through a commissure such that a lower ring of the helix ring is positioned below the heart valve in the ventricle, and an upper ring of the helix ring is positioned in the atrium, trapping the heart valve tissue therebetween.

3. Method according to claim 1, wherein the catheter has a distal end and a proximal end, the method comprising
   engaging a pre-determined cardiac structure with a coupling device arranged at the distal end to couple and align the catheter in a determined direction in the heart, and
   deploying the annuloplasty implant through the catheter.

4. Method according to claim 3, wherein aligning the catheter in a determined direction in the heart comprises anchoring the catheter relative to the pre-determined cardiac structure.

5. Method according to claim 3, wherein the coupling device comprises a commissure locator device, the method comprising locating the position of the commissures of a heart valve by positioning the commissure locator device at the commissures.

6. Method according to claim 3, wherein the port is angled in a direction towards the pre-determined cardiac structure.

7. Method according to claim 3, wherein the port is angled in a direction towards the coupling device.

8. Method according to claim 3, wherein the coupling device is extendable relative the distal end of the catheter.

9. Method according to claim 3, wherein the coupling device comprises at least one radially expandable superior loop and at least one radially expandable inferior loop, wherein the superior loop contacts a superior surface at the pre-determined cardiac structure and the inferior loop contacts an inferior surface at the pre-determined cardiac structure when the loops are in an expanded position to capture a portion of the pre-determined cardiac structure between the inferior and superior loops.

10. Method according to claim 1, comprising delivering an interventional heart device, other than said annuloplasty implant, through said catheter.

11. Method according to claim 10, wherein the interventional heart device or the annuloplasty implant is deployed through a port on the catheter.

12. Method according to claim 11, wherein the port is angled in a direction towards the pre-determined cardiac structure.

13. Method according to claim 11, wherein the port is angled in a direction towards the coupling device.

14. Method according to claim 1, wherein activating the displacement unit in an activated state comprises state comprises positioning a proximal expandable portion against a tissue wall at the entrance of the CS, positioning a distal anchoring portion inside the CS, activating the displacement unit in an activated state whereby the distal anchoring portion is moved in a longitudinal direction of the displacement unit to reduce the distance between the distal anchoring portion and the proximal expandable portion such that the shape at the annulus is modified to said modified shape.

15. Method according to claim 1, comprising guiding the annuloplasty implant into place at the annulus by a guide positioned at the catheter.

16. Method according to claim 1, comprising providing a pre-loaded clip in a stapling device, and delivering the clip from the stapling device to a target site to fix the annuloplasty implant to tissue at the target site, whereupon delivering the clip to the target site the clip strives to the relaxed shape and applies a compressive force to the tissue and/or annuloplasty implant for fixating the tissue and/or annuloplasty implant.

* * * * *